(12) United States Patent
Torrie

(10) Patent No.: US 9,895,165 B2
(45) Date of Patent: Feb. 20, 2018

(54) SURGICAL NEEDLE

(71) Applicant: Smith & Nephew, Inc., Memphis, TN (US)

(72) Inventor: Paul Alexander Torrie, Marblehead, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/776,940

(22) PCT Filed: Mar. 14, 2014

(86) PCT No.: PCT/US2014/028504
§ 371 (c)(1),
(2) Date: Sep. 15, 2015

(87) PCT Pub. No.: WO2014/144200
PCT Pub. Date: Sep. 18, 2014

(65) Prior Publication Data
US 2016/0022311 A1 Jan. 28, 2016

Related U.S. Application Data

(60) Provisional application No. 61/791,398, filed on Mar. 15, 2013.

(51) Int. Cl.
| A61B 17/34 | (2006.01) |
| A61M 25/06 | (2006.01) |
| A61B 17/00 | (2006.01) |

(52) U.S. Cl.
CPC ...... *A61B 17/3472* (2013.01); *A61B 17/3494* (2013.01); *A61B 17/3496* (2013.01);
(Continued)

(58) Field of Classification Search
CPC ............ A61B 17/3415; A61B 17/3401; A61B 2018/1425; A61B 2018/005577; A61B 2018/00434; A61B 17/3496; A61B 17/3472; A61B 17/34945; A61B 2018/00577; A61B 2017/2945; A61B 17/3494; A61B 2017/00862; A61B 2017/00964; A61B 2017/3454;
(Continued)

(56) References Cited

U.S. PATENT DOCUMENTS

| 1,527,291 A | 7/1923 | Zorraquin |
| 2,623,521 A | 12/1952 | Shaw |
(Continued)

FOREIGN PATENT DOCUMENTS

| CN | 2553748 A | 6/2003 |
| CN | 101730506 A | 6/2010 |
(Continued)

OTHER PUBLICATIONS

Office Action from related Japanese Application No. 2015-500561 issued Dec. 19, 2016.
(Continued)

*Primary Examiner* — Manuel Mendez
(74) *Attorney, Agent, or Firm* — Norman F. Hainer, Jr.

(57) ABSTRACT

The disclosure provides examples of a surgical needle for entering a joint space, such as the hip joint, through tissue.

17 Claims, 28 Drawing Sheets

(52) U.S. Cl.
CPC . *A61M 25/065* (2013.01); *A61B 2017/00862* (2013.01); *A61B 2017/00964* (2013.01); *A61B 2017/3454* (2013.01); *A61M 2210/005* (2013.01)

(58) Field of Classification Search
CPC .................. A61B 17/34; A61M 19/00; A61M 2025/0089; A61M 25/007; A61M 5/3291; A61M 25/065; A61M 2210/005; A61N 1/05; A61N 1/3606
See application file for complete search history.

(56) References Cited

U.S. PATENT DOCUMENTS

| | | | |
|---|---|---|---|
| 5,104,381 A | | 4/1992 | Gresl |
| 5,137,509 A | | 8/1992 | Freitas |
| 5,320,608 A | | 6/1994 | Gerrone |
| 5,401,247 A | * | 3/1995 | Yoon .................. A61B 10/0233 604/164.12 |
| 5,509,910 A | * | 4/1996 | Lunn .................. A61M 25/001 604/264 |
| 5,569,288 A | | 10/1996 | Yoon |
| 5,573,511 A | | 11/1996 | Yoon |
| 5,578,053 A | | 11/1996 | Yoon |
| D379,515 S | | 5/1997 | Kuehn et al. |
| 6,001,084 A | | 12/1999 | Rick et al. |
| 6,071,292 A | | 6/2000 | Makower et al. |
| 6,270,484 B1 | * | 8/2001 | Yoon .................. A61B 17/3494 604/264 |
| 6,656,160 B1 | | 12/2003 | Johnson et al. |
| 6,837,878 B2 | | 1/2005 | Smutney et al. |
| 8,202,251 B2 | | 6/2012 | Bierman et al. |
| 2002/0099335 A1 | * | 7/2002 | Zohmann ........... A61B 17/3401 604/198 |
| 2003/0220677 A1 | * | 11/2003 | Doan ..................... A61N 1/056 607/122 |
| 2004/0133124 A1 | | 7/2004 | Bates et al. |
| 2004/0171986 A1 | | 9/2004 | Tremaglio, Jr. et al. |
| 2004/0225180 A1 | | 11/2004 | Junger |
| 2005/0159762 A1 | | 7/2005 | Nuutinen |
| 2006/0089609 A1 | | 4/2006 | Bleich et al. |
| 2007/0038230 A1 | | 2/2007 | Stone |
| 2007/0225562 A1 | | 9/2007 | Spivey |
| 2008/0188928 A1 | | 8/2008 | Salahieh et al. |
| 2009/0157099 A1 | | 6/2009 | Surti |
| 2009/0163934 A1 | | 6/2009 | Raschdorf et al. |
| 2009/0275970 A1 | | 11/2009 | Leibowitz |
| 2009/0287236 A1 | | 11/2009 | Bakos et al. |
| 2009/0299400 A1 | | 12/2009 | Wayman et al. |
| 2010/0036361 A1 | | 2/2010 | Nguyen et al. |
| 2010/0113873 A1 | | 5/2010 | Suzuki et al. |
| 2010/0160731 A1 | | 6/2010 | Giovannini et al. |
| 2010/0249750 A1 | * | 9/2010 | Racz .................. A61B 17/3478 604/512 |
| 2011/0082538 A1 | | 4/2011 | Dahlgren et al. |
| 2011/0218485 A1 | | 9/2011 | Tran et al. |
| 2011/0224742 A1 | | 9/2011 | Weisel et al. |
| 2011/0257581 A1 | | 10/2011 | Koziczynski et al. |
| 2013/0211427 A1 | | 8/2013 | Castell |
| 2015/0080924 A1 | | 3/2015 | Stulen |

FOREIGN PATENT DOCUMENTS

| | | |
|---|---|---|
| EP | 2149339 A2 | 1/2010 |
| EP | 2277457 A1 | 1/2011 |
| EP | 2907466 | 8/2015 |
| GB | 2064963 A | 6/1981 |
| GB | 2397235 A | 7/2004 |
| JP | S56-101305 U | 8/1981 |
| JP | H08-511711 A | 12/1996 |
| JP | H09-103433 A | 4/1997 |
| JP | 2012179087 A | 9/2012 |
| JP | 2013013592 A | 1/2013 |
| SU | 1232236 A1 | 5/1986 |
| SU | 1303149 A1 | 4/1987 |
| SU | 1560143 A1 | 4/1990 |
| WO | 94/06681 A3 | 11/1994 |
| WO | 95/00189 | 1/1995 |
| WO | 2001006938 A1 | 2/2001 |
| WO | 2009114833 A1 | 9/2009 |
| WO | 2012006161 A2 | 1/2012 |
| WO | 2012096816 A1 | 7/2012 |
| WO | 2015193881 | 12/2015 |

OTHER PUBLICATIONS

International Preliminary Report for corresponding PCT Application No. PCT/US14/028504 mailed Sep. 24, 2015.
First Office Action and Search Report from related Chinese Application No. 2013800250782 issued Jun. 2, 2016.
Office Action from related Russian Application No. 2014136479/14(059050) issued Dec. 27, 2016.
Office Action from related Chinese Application No. 201380025078.2 issued Feb. 7, 2017.
Russian Office Action dated Mar. 23, 2017 for Application No. RU 2014136479.
Japanese Office Action dated Jun. 12, 2017 for Application No. JP 2015-500561.
International Preliminary Report on Patentability from related Application No. PCT/US2016/018234 dated Aug. 22, 2017.
Search Report and Written Opinion from corresponding International Application No. PCT/US2017/049131, dated Oct. 11, 2017.

* cited by examiner

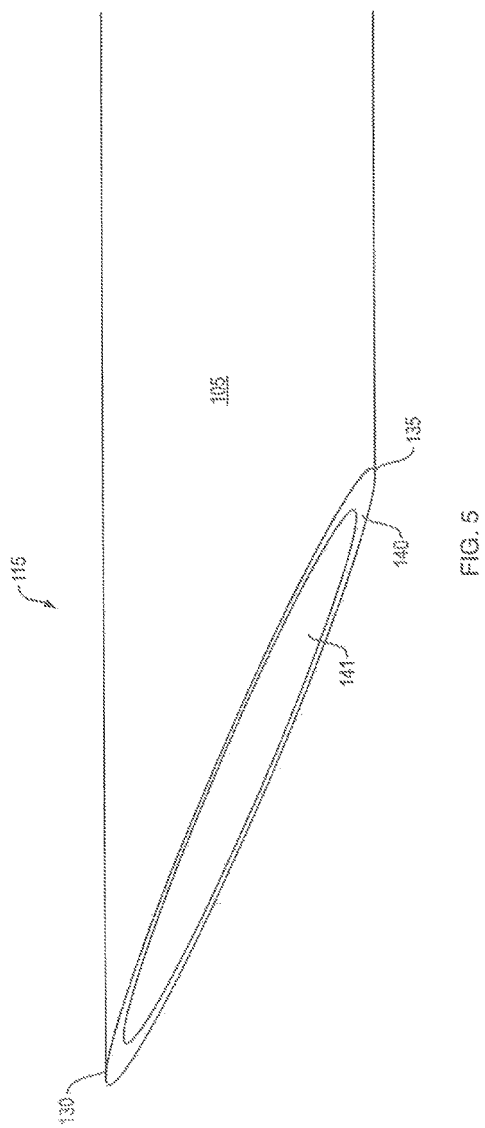

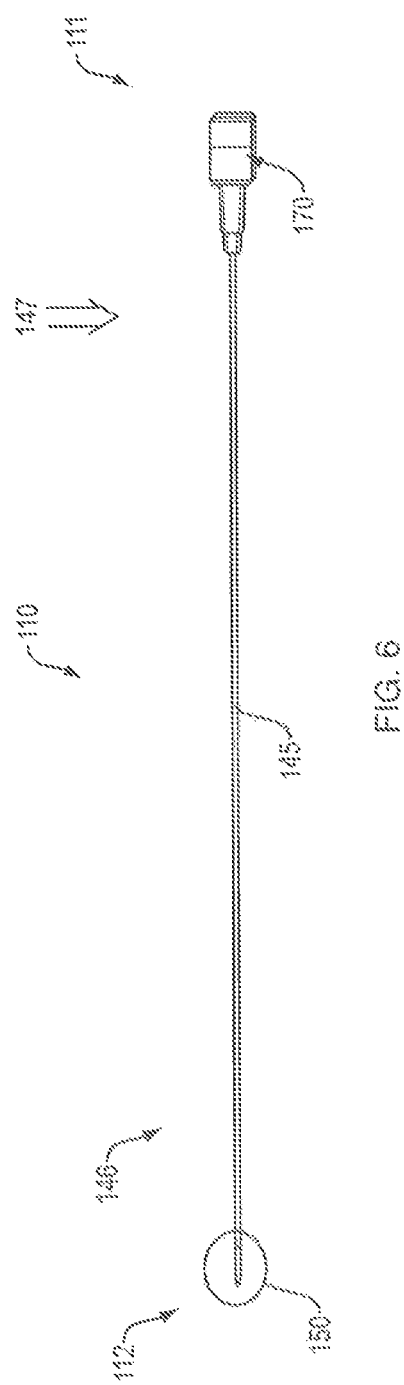

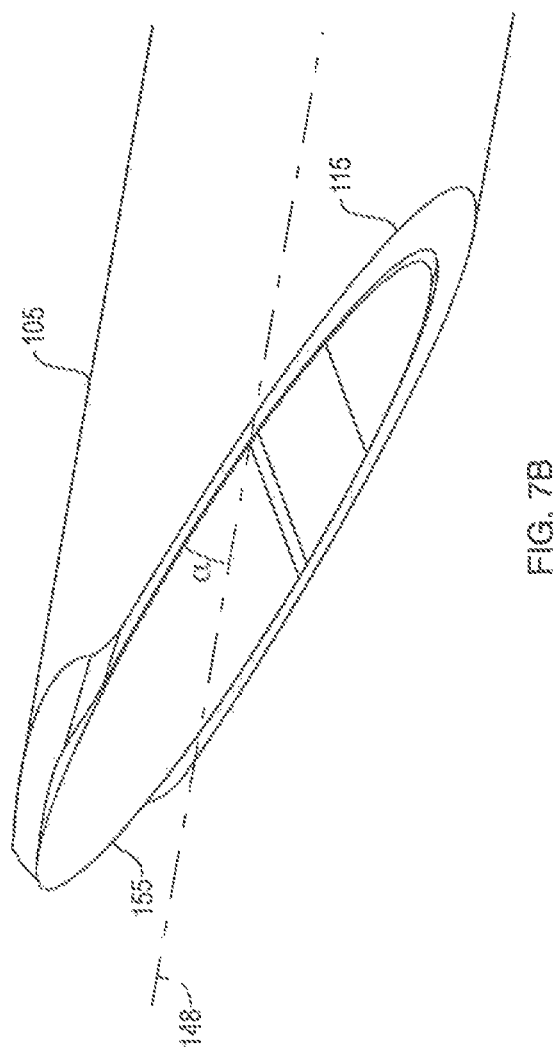

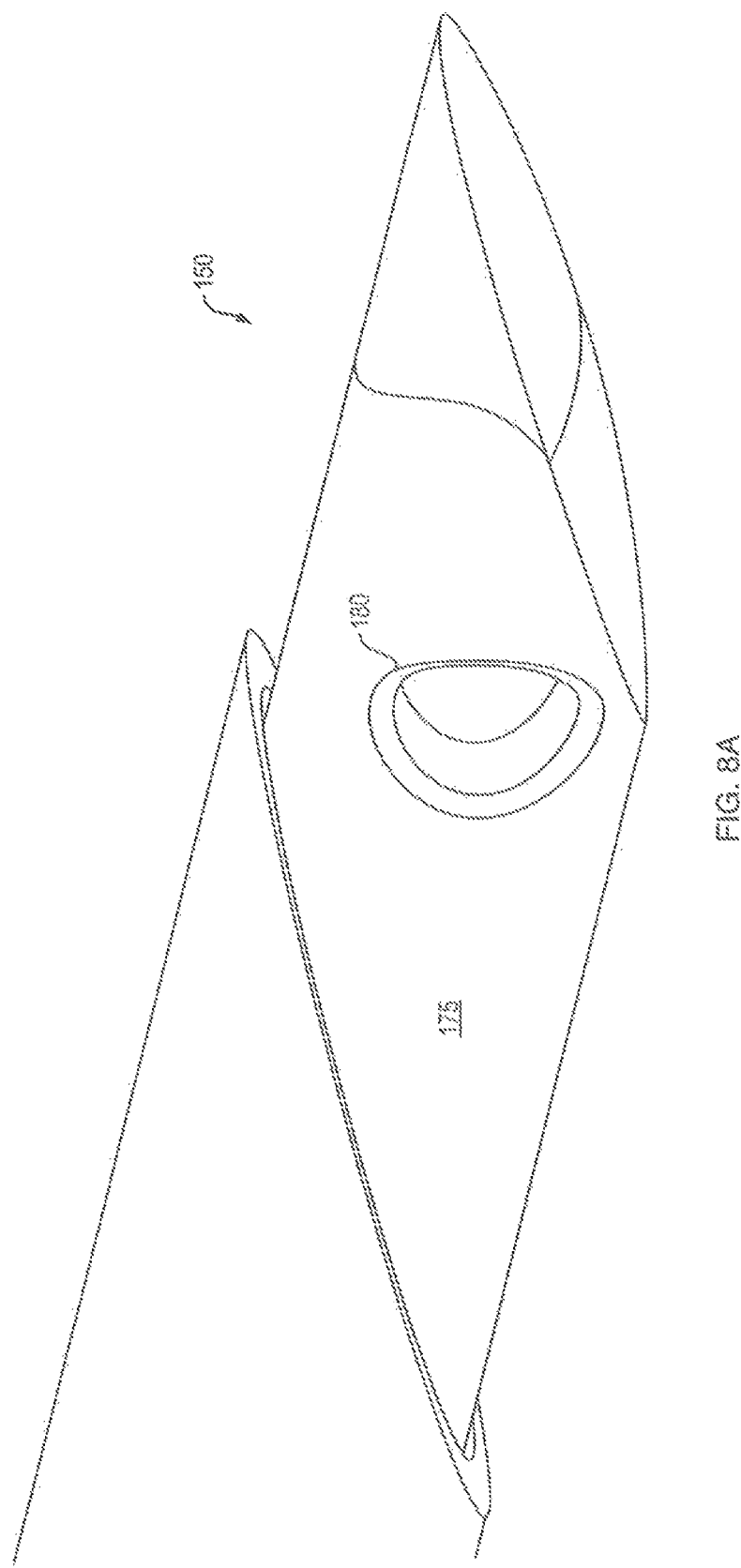

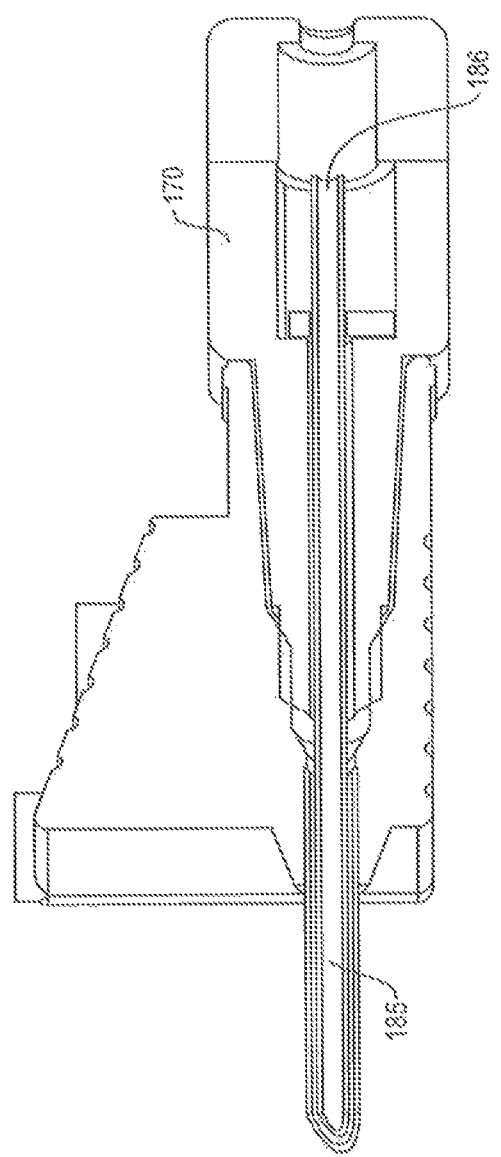

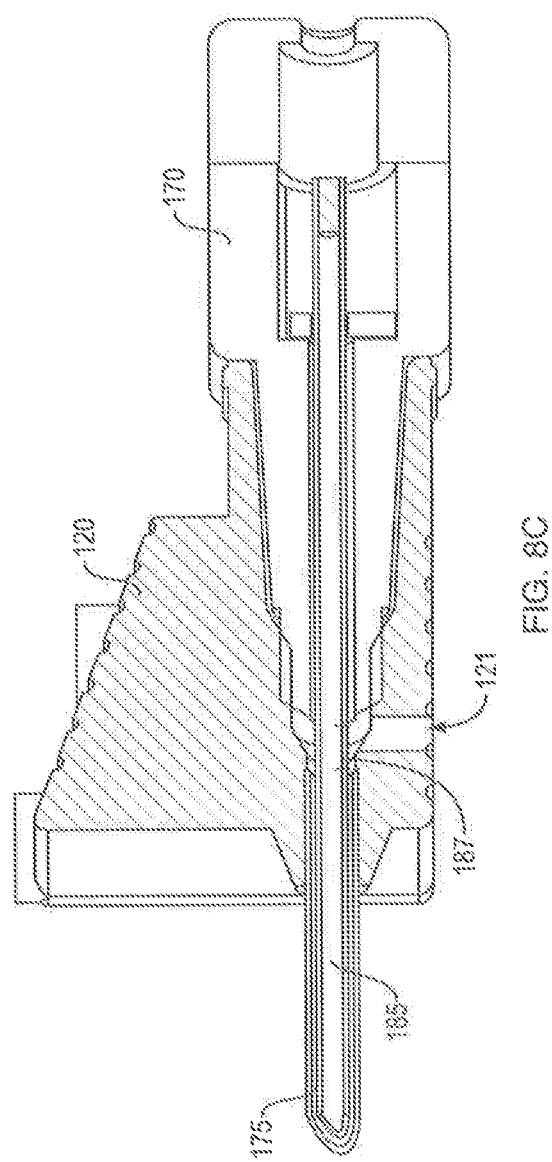

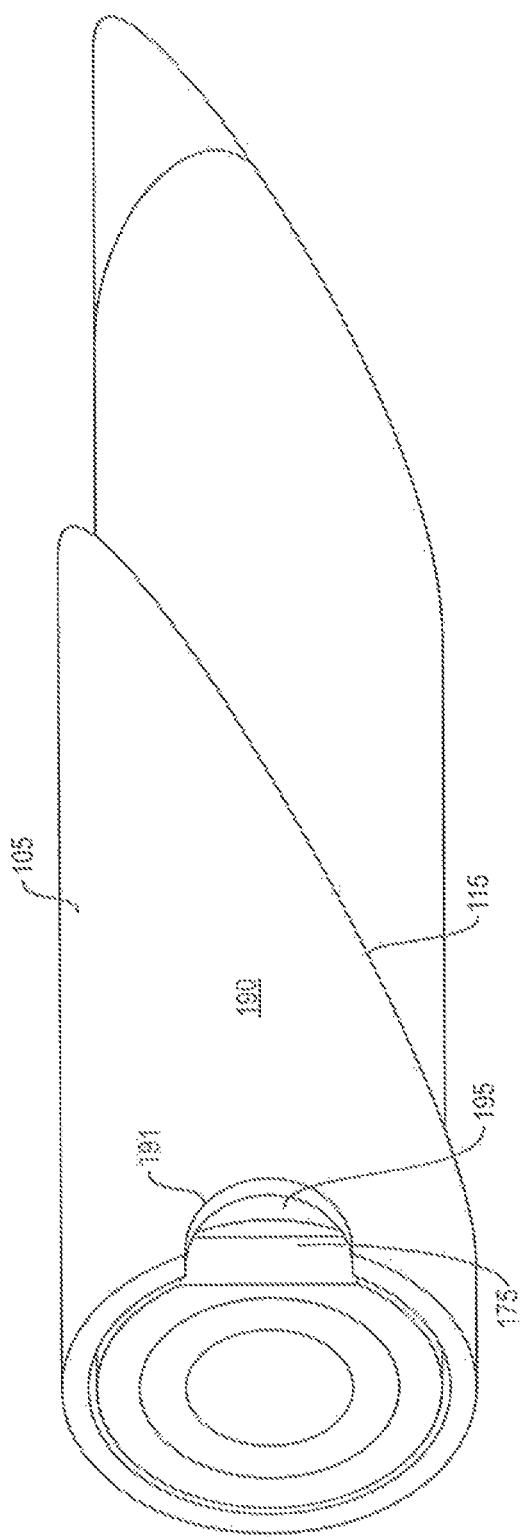

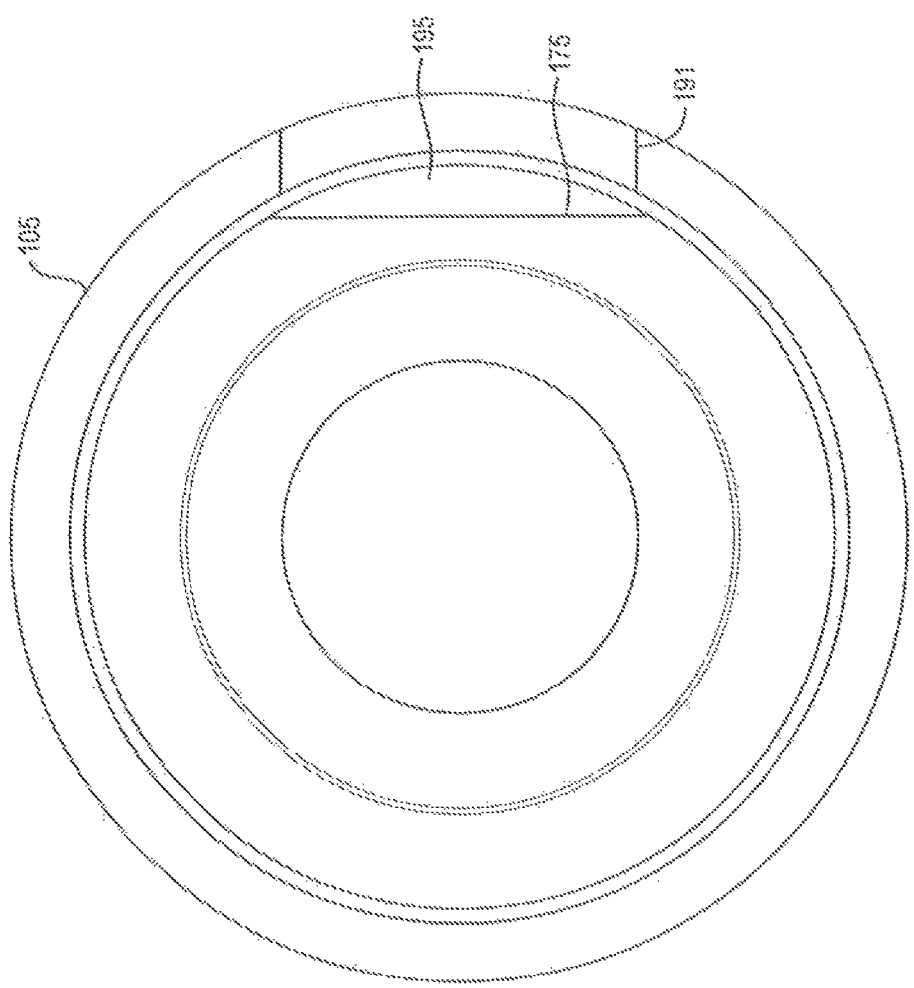

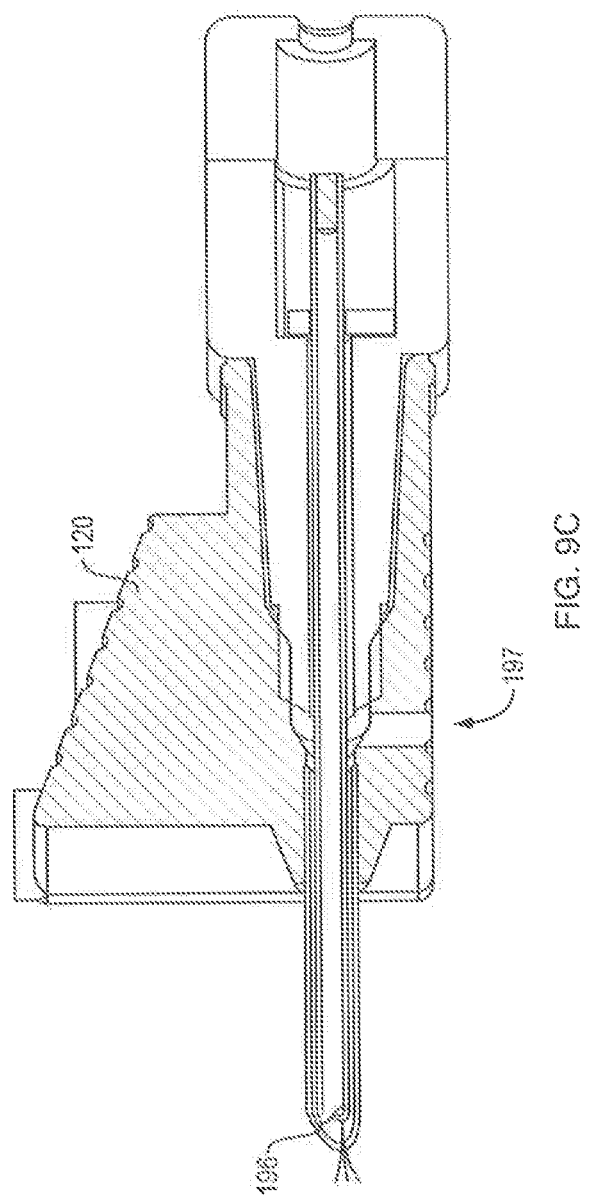

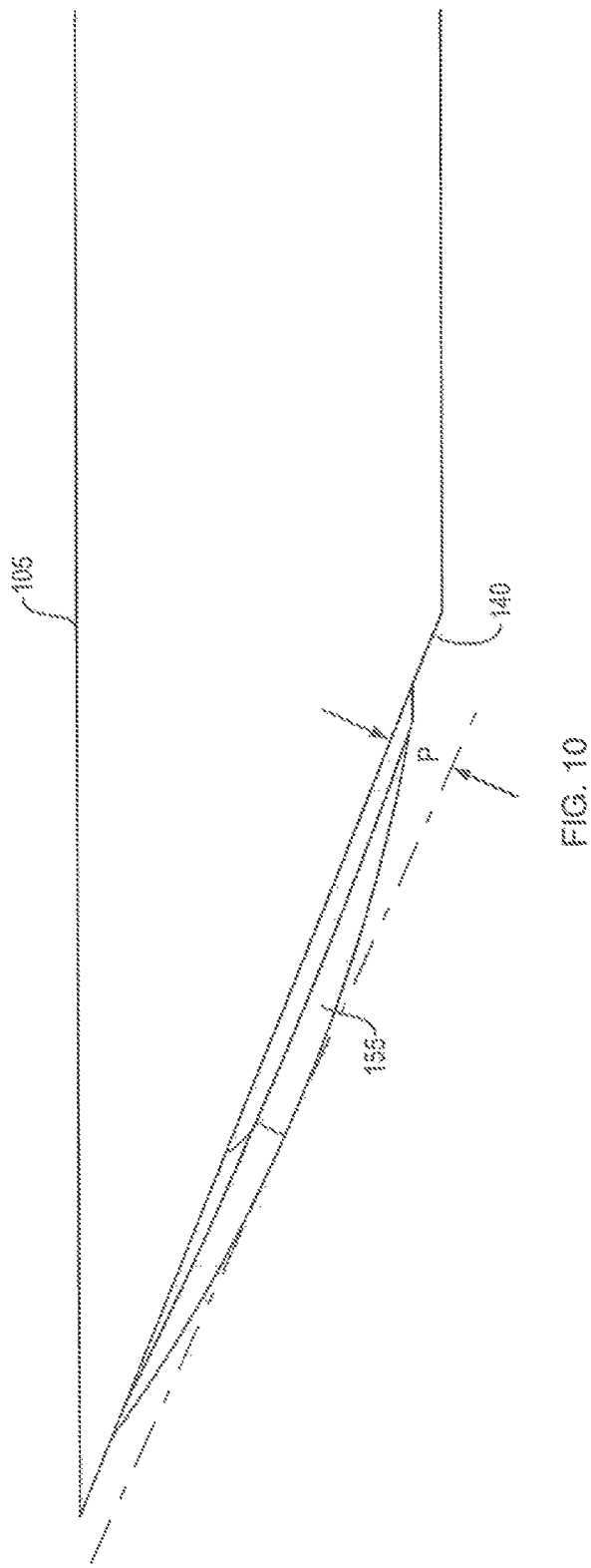

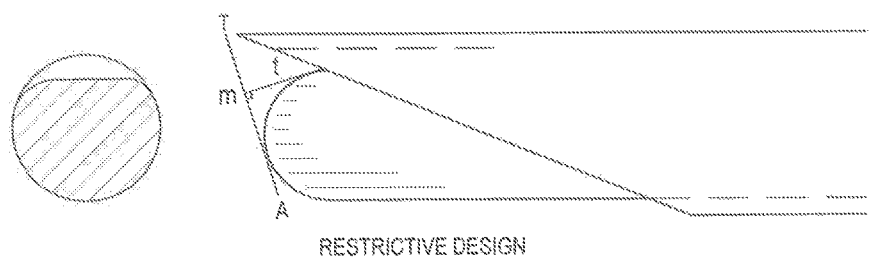
RESTRICTIVE DESIGN
LENGTHS
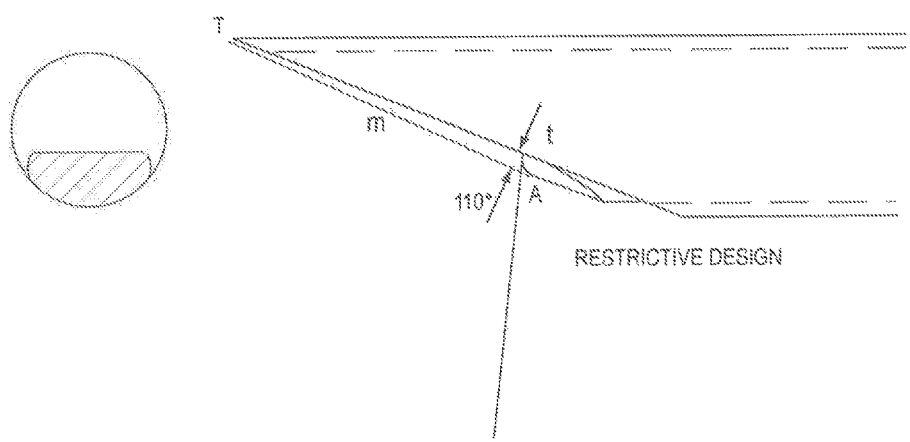
RESTRICTIVE DESIGN
FIG. 12A

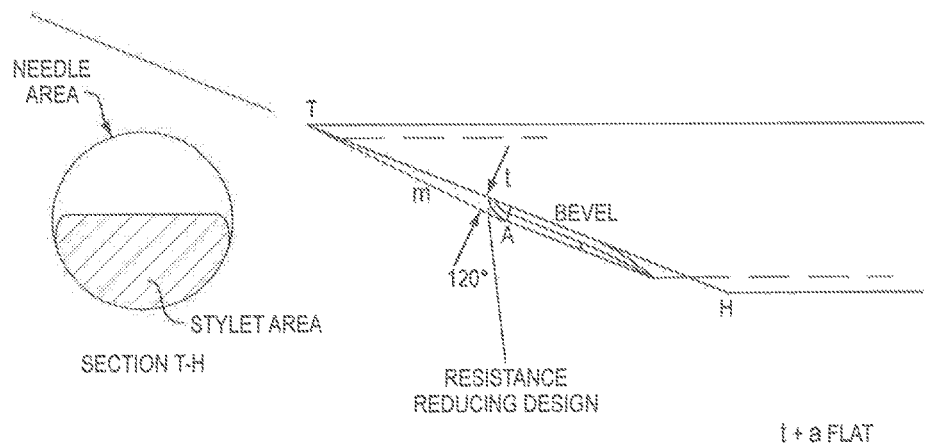
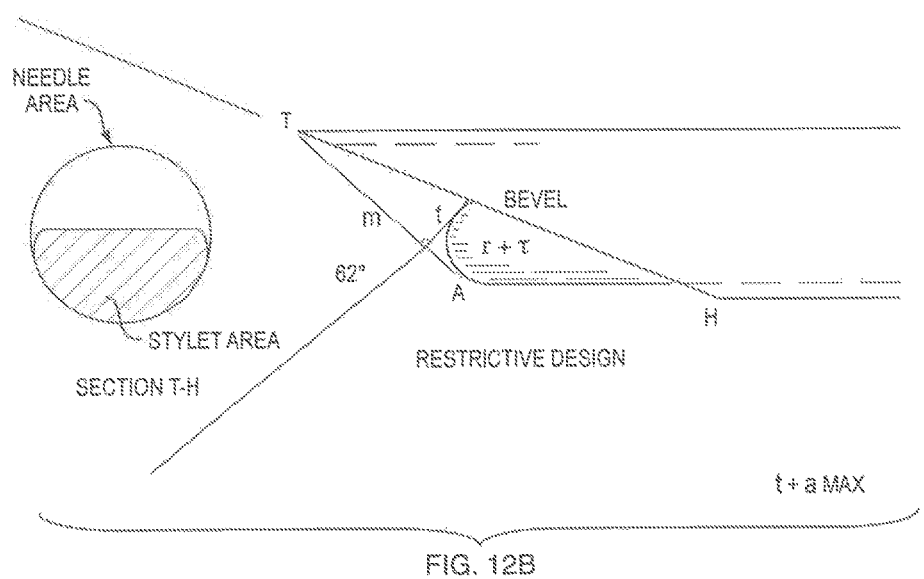
FIG. 12B

SURGICAL NEEDLE

CROSS-REFERENCE TO RELATED APPLICATION(S)

This is a U.S. national phase application and claims priority to International Application No. PCT/US14/28504, filed on Mar. 14, 2014. The PCT/US14/28504 application claims the benefit of U.S. Provisional Application No. 61/791,398, filed on Mar. 15, 2013, and entitled, "Surgical Needle," the entire teachings of the above applications are incorporate herein by reference.

BACKGROUND

Arthroscopic surgery is a minimally invasive surgical procedure in which examination and treatment of damage to the interior of a joint is performed using an arthroscope, a type of endoscope that is inserted into the joint through a small incision. To access the interior of the joint, the surgeon creates arthroscopic portals and inserts cannulas through the patient's skin and through intervening layers of tissue and ligaments. The surgeon then introduces arthroscopic instruments through these access portals to perform the surgery. Creating access portals can be extremely challenging for the surgeon.

Creating access portals in hip arthroscopy, especially the first portal can be problematic. The surgeon carries out the first portal blind under 2D fluoroscopic imaging with no direct visualization through an arthroscope. Studies show that a majority of iatrogenic damage is created in the femoral head by the initial blind needle placement. Other problems arise from some of the hip structures, such as the articular cartilage on the femoral head, which is quite delicate. The surgeon must be careful when forming the access portal so as to not to these structures.

The capsule surrounding the hip joint is of particular concern. The capsule is leather-like being significantly denser and "tougher" than tissue externally surrounding the capsule. Even with a sharp needle, the surgeon must push relatively hard to pierce the capsule. However, the capsule is thin so the surgeon risks popping through the capsule, uncontrollably, and accidently damaging tissue beyond the capsule.

In view of the problems described above, there is a need to minimize the damage created by blind placement of the needle. More specifically, there is a need to control the penetration of the periarticular soft tissues and hip capsule by a needle without visual aid. These needs are addressed by a surgical needle with a movable stylet having a deformable tip. The stylet rapidly extends beyond a tip of a bevel of the surgical needle when the surgical needle does not have tissue pressing against its distal end. For example, the stylet extends just after the surgical needle exits the capsule but before contacting the femoral head. In case the stylet contacts the femoral head, accidently, the deformable tip inhibits damage to the femoral head.

SUMMARY

In one aspect, at least one example described herein provides a surgical needle for entering a joint space through tissue. The surgical needle includes a hollow body with a bevel. A periphery of the bevel defines an open area at the bevel. The surgical needle further includes a stylet movable within the hollow body between an extended position and retracted position. The stylet includes an elongated body having a distal region and a proximal region. The elongated body comprises a non-deformable first material. The stylet further includes a tip formed with the elongated body. The tip extends from the distal region of the elongated body and terminates at a distal terminus. The stylet further includes a taper extending between the distal terminus and a point proximal to the distal terminus. At least a portion of the taper fills in the open area at the bevel when the stylet is in the retracted position. The tip includes a first portion extending a longitudinal length, distally, from the distal region of the elongated body and terminating at a distal facing surface. The tip further includes a second portion extending between the distal facing surface and the distal terminus. The second portion comprises a deformable second material.

In another example, the surgical needle may further include one or more of the following, alone or in any combination. The non-deformable first material may be any one of metal and non-metal. The deformable second material may be reversibly deformable. The reversibly deformable second material may be an elastomer. In one example, the first portion and second portion of the tip comprise an elastomeric material.

A portion of the taper may project, distally, beyond the periphery of the bevel when the stylet is in the retracted position. Alternatively, the taper may be flush with the periphery of the bevel when the stylet is in the retracted position. The taper may be at an acute angle to a longitudinal axis extending between the distal region and the proximal region of the elongated body.

In some examples, the second portion of the tip includes a proximal facing surface in contact with the distal facing surface of the first portion of the tip. In other examples, the distal facing surface of the first portion and the second portion are bonded together with an adhesive. In still other examples, the second portion is molded over the distal facing surface of the first portion.

Examples of the surgical needle may further include a needle hub disposed at an end of the hollow body opposite the bevel and a stylet hub disposed at the proximal region of the elongated body. The stylet hub and needle hub cooperatively couple the stylet and the hollow body together.

Other examples of the surgical needle may further include a lumen through the elongated body. The lumen is opened at the proximal region of the elongated body and closed at the distal region of the elongated body. The examples further include an outer surface extending between the proximal region and the distal region of the elongated body, and a port in the outer surface and adjacent to the tip. The port is in fluid communication with the lumen which permits joint fluid to flow into the lumen at the distal region of the elongated body and flow out of the lumen at the proximal region of the elongated body. Some of the examples further include a needle hub and stylet hub, as described herein. The needle hub includes an aperture in fluid communication with the lumen at the proximal region of the elongated body which permits fluid to drain out from the surgical needle. Alternatively, the stylet hub comprises an aperture in fluid communication with the lumen at the proximal region of the elongated body which permits fluid to drain out from the surgical needle.

An example of the surgical needle further includes an outer surface extending a partial length, distally, from the proximal region of elongated body. The outer surface of the stylet and an inner surface of the hollow body form a fluid conduit. The hollow body further includes a port in an outer surface of the hollow body and adjacent to the bevel. The port is in fluid communication with the fluid conduit which permits joint fluid to flow into the fluid conduit at the distal region of the elongated body and flow out of the fluid conduit at the proximal region of the elongated body. The outer surface of the stylet may include a flat formed in the outer surface of the stylet.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The foregoing and other objects, features, and advantages will be apparent from the following more particular description of the embodiments as illustrated in the accompanying drawings in which like reference characters refer to the same parts throughout the different views. The drawings are not necessarily to scale, emphasis instead being placed upon illustrating the principles, characteristics, and features of the embodiments. In the drawings:

FIG. 5 is a close up view of a bevel at the distal end of the hollow body.

FIG. 6 is a side view of an example of the stylet with a deformable tip.

FIGS. 7A and 7B show an example of the deformable tip when the stylet is in a extended position and retracted position.

FIGS. 8A-8C are side views of an example of the surgical needle for conducting fluid from a joint space to outside the patient.

FIGS. 9A-9C are side views of another example of the surgical needle for conducting fluid from a joint space to outside the patient.

FIG. 10 is a side view of an example of the surgical needle having a stylet tip projecting away from the bevel when the stylet is in the retracted position.

FIGS. 12A-12E shows examples of resistance reducing and resistive design.

DETAILED DESCRIPTION

The following description of examples is in no way intended to limit the disclosure, its application, or uses.

Figure 1:
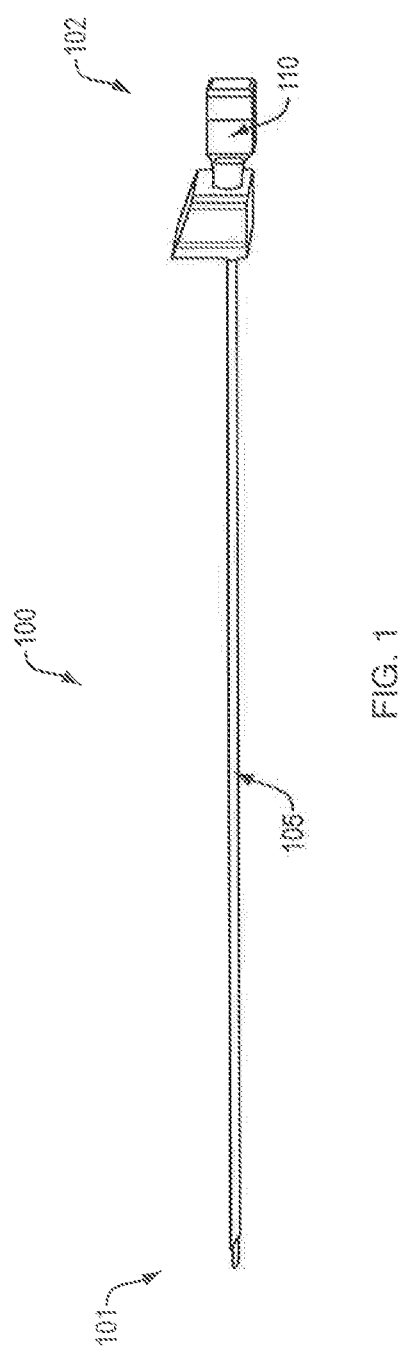
FIG. 1 is a side view of an example surgical needle having a hollow body and stylet.
Figure 2:
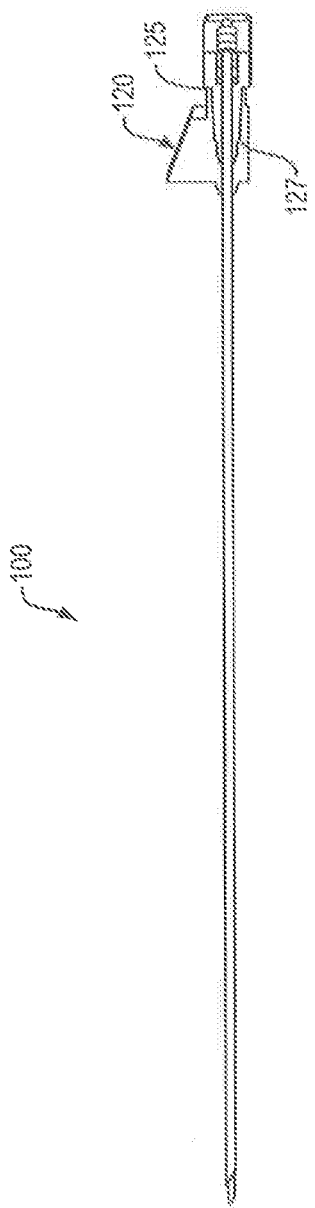
FIG. 2 is a cross-sectional view of the example surgical needle of FIG. 1.

FIGS. 1 and 2 show an example surgical needle 100 for creating portals for joint arthroscopy through which an arthroscopy and/or surgical instruments enter. The surgeon inserts the surgical needle 100 into, for example, the patient's hip joint. This can be done blind without direct visualization by the surgeon. The surgical needle 100 has a distal end 101 that is inserted into the patient and a proximal end 102 that is manipulated by the surgeon to move and, rotate the surgical needle 100. The surgical needle 100 has a hollow body 105 and stylet 110 movable within the hollow body 105 (best seen in FIG. 2). As the surgeon moves the surgical needle 100, the stylet 110 moves between a retracted position, extended position, and positions in between (described in greater detail below).

Figure 3:
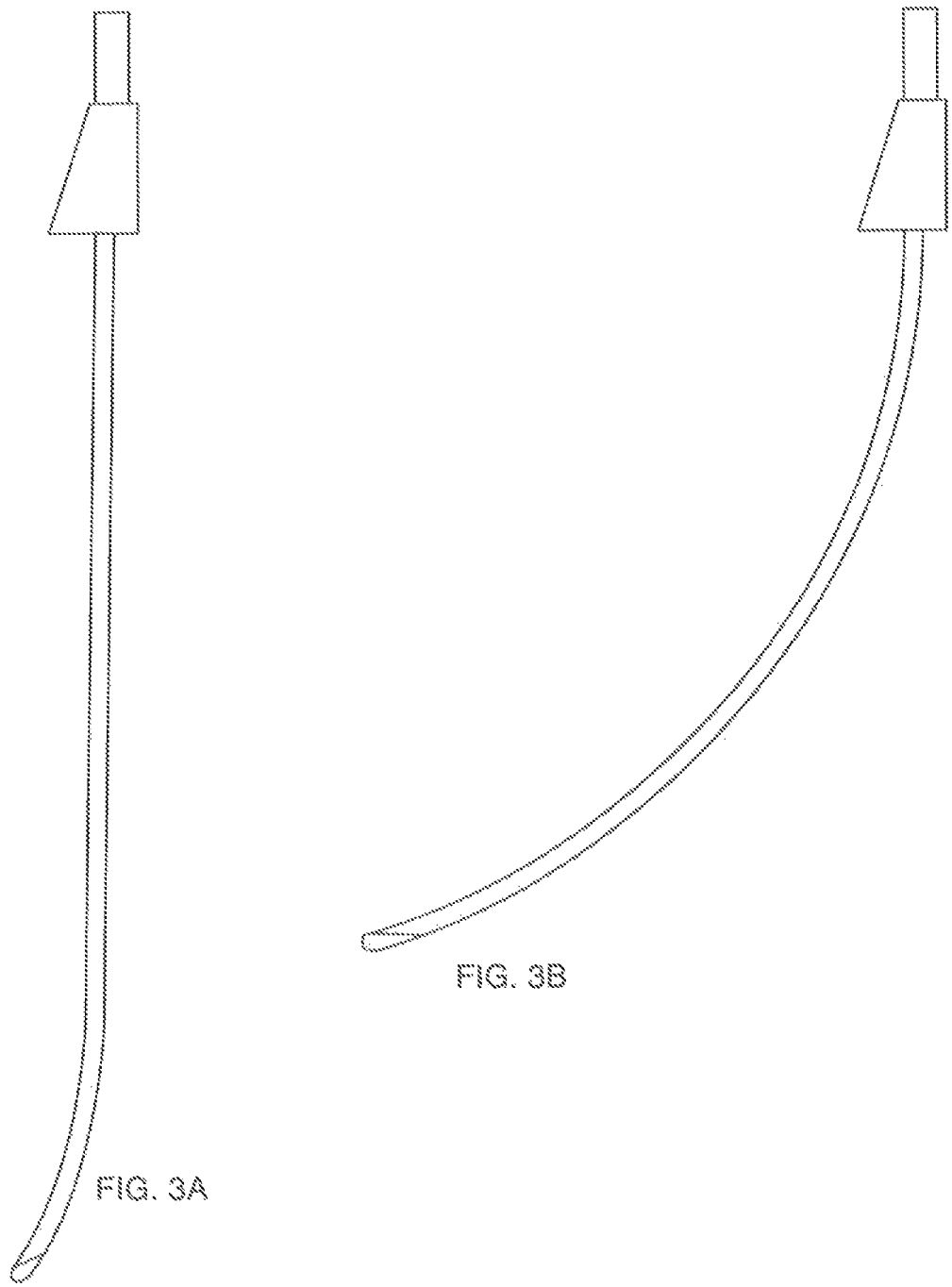
FIGS. 3A and 3B are views of examples of a curved surgical needle.
Figure 4:
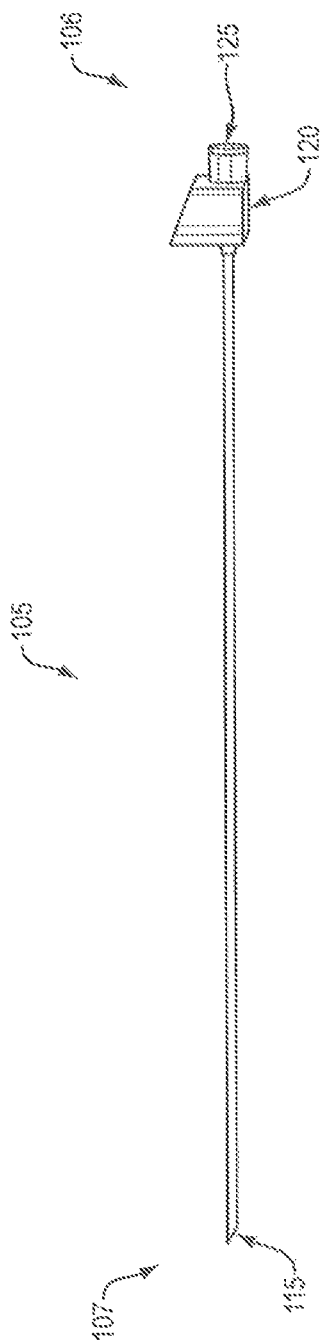
FIG. 4 is a side view of an example of the hollow body.

FIGS. 3A and 3B show examples of the surgical needle 100 that are curved in shape. FIG. 4 shows an example of the hollow body 105. The hollow body 105 has a proximal end 106 and distal end 107. Disposed at the proximal end 106 of the hollow body 105 is a needle hub 120. The needle hub 120 has an opening 125 at an end opposite the hollow body 105. The opening 125 defines a passageway 127 inside of the needle hub 120 (best seen in FIG. 2). The passageway 127 is in communication with the interior of the hollow body 105. The passageway 127 and the interior define a continuous volume that is opened at a bevel 115 at the distal end 101 of the surgical needle 100 and at the opening 125 at the proximal end 102 of the surgical needle 100. In some examples of the surgical needle 100, the opening 125 and passageway 127 are used to couple the hollow body 105, and stylet 110 together (described in greater detail below.

FIG. 5 shows an example of the bevel 115 at the distal end 107 of the hollow body 105. The bevel 115 includes at the most distal end, a tip 130 for cutting/penetrating tissue and at the most proximal end, a heel 135. A periphery of the bevel or "face" 140 extends between the tip 130 and heel 135. The face 140 supports the tip 130. The face 140 may or may not be configured to cut/penetrate tissue. Furthermore, a portion of the face 140 may cut/penetrate tissue while another portion may not. The face 140 defines an open area 141 at the bevel 115.

With the stylet 110 in the retracted position, the tip 130 is the first to encounter the tissue and then the face 140. As the surgeon pushes the surgical needle 100 through the tissue, more of the face 140 encounters the tissue and, the resistance through the tissue increases. The surgeon feels this increase in resistance through the surgical needle 100 and pushes the surgical needle 100 harder.

As the surgeon moves the surgical needle 100 through tissue, the surgeon feels different levels of resistance. For example, the resistance felt by the surgeon when the surgical needle 100 enters the tissue is different than the resistance felt by the surgeon when the surgical needle 100 exits the tissue. In this way, the surgeon can determine the progress of the surgical needle 100 by the tactile feedback provided (transmitted) by the surgical needle 100.

Figure 7A:
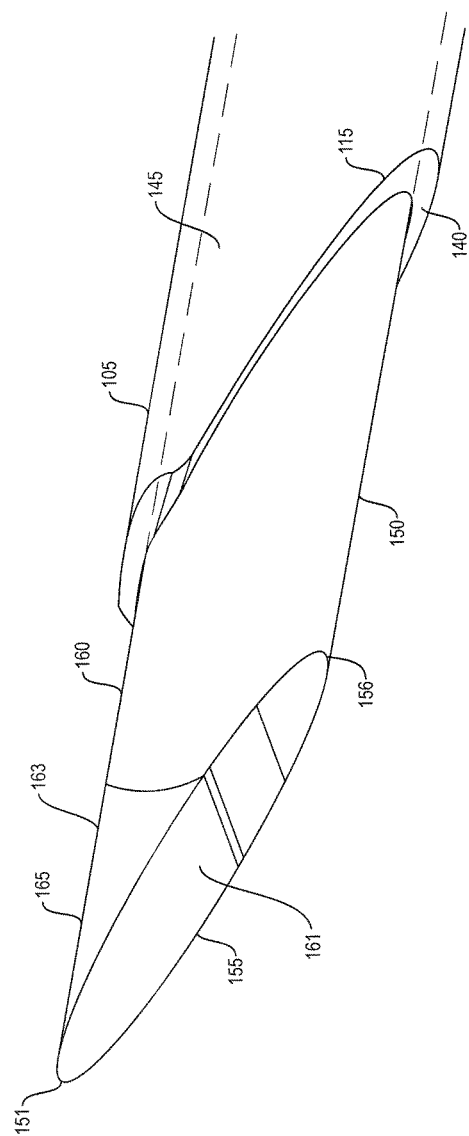

FIG. 6 shows an example of the stylet 110 with an elongated body 145 and tip 150. The elongated body 145 is made from a non-deformable first material, such as metal or non-metal. An example of the elongated body 145 is made from a plastic suitable for surgical use. A portion of the tip 150 is made from a deformable second material. In some examples of the stylet 110, the elongated body 145 and stylet tip 150 are separate components that are bonded or molded together. In other examples of examples of the stylet 110, the elongated body 145 and stylet tip 150 are formed together. When the stylet 110 is in the extended position, the stylet tip 150 is moved distally and inhibits the tip 130 (of FIG. 5) from touching joint surfaces. In case the stylet tip 150 contacts tissue when it is in the extended position, a portion of the tip deforms. In turn, the deformation of the tip inhibits damage to the tissue. FIGS. 7A and 7B show an example of the stylet 110 in the extended position and the retracted position, respectively. The elongated body 145 has a distal region 146 and a proximal region 147 (shown in FIG. 6). The tip 150 extends from the distal region 146 of the elongated body 145 and terminates at a distal terminus 151. A taper 155 extends between the distal terminus 151 and a point 156 proximal to the distal terminus 151. At least a portion of the taper 155 fills in the open area 141 at the bevel 115 (of FIG. 5) when the stylet 110 is in the retracted position.

The stylet tip 150 includes a first portion 160 and second portion 165. The first portion 160 extends a longitudinal length, distally, from the distal region 146 of the elongated body 145 and terminates at a distal facing surface 161. The second portion 165 extends between the distal terminus 151 and the distal facing surface 161. In the example shown in FIGS. 7A and 7B, the distal facing surface is planar surface. Other examples of the distal facing surface include a threaded recess, threaded stud, key, keyway and other structures suitable for joining the first portion 160 and second portion 165.

In a convenient example of the stylet tip 150, the second portion 165 is made from a reversibly deformable second material, such as an elastomer or other material with a time dependent deformation. In another example of the tip 150, the material for the second portion 165 is selected based on determining a degree (or range) of deformation that inhibits (or at least minimizes) damage to hard tissue, soft tissue, etc. Further consideration is given to the suitability of using such a material in surgery (e.g., the ability to be sterilized).

In one example of the stylet tip 150, both the first portion 160 and second portion 165 comprise an elastomeric material. In another example of the tip 150, the first portion 160 is made from the same non-deformable first material as the elongated body 145. In yet another example of the tip 150, the first portion 160 is made from a non-deformable material different from the non-deformable material from which the elongated body 145 is made. In still yet another example of the tip 150, the choice of material for the first portion 160 depends on a material chosen for the second portion 165.

In a convenient example, the second portion 165 of the stylet tip 150 is bonded to the distal facing surface 161 of the first portion 160 with an adhesive or other suitable bonding agent. In another example, the second portion 165 is molded over the distal facing surface 161 of the first portion 160. In still another example, the second portion 165 is molded over the distal facing surface 161 as well as other surface(s) of the first portion 160 that are adjacent to the distal facing surface 161.

It should be readily apparent that other approaches and techniques for joining the distal facing surface 161 of the first portion 160 and the second portion 165 are contemplated by the present disclosure. For example, the second portion 165 includes a proximal facing surface 163 that is in contact with the distal facing surface 161 of the first portion 160. An example of a mechanical approach uses female and male threaded parts, or a key and keyway to join the distal facing surface 161 of the first portion 160 and the second portion 165. In yet another example, the distal facing surface 161 of the first portion 160 and the second portion 165 are joined using an insert molding technique.

In some examples of the surgical needle 100, the taper 155 is flush with the periphery (face) 140 of the bevel 115 when the stylet 110 is in the retracted position, as shown in FIG. 7B. In a convenient example of the surgical needle 100, the taper 155 is at an acute angle "α" to a longitudinal axis 148 that extends between the distal region 146 and the proximal region 147 of the elongated body 145. In some examples, the angle α and an angle of the bevel 115, as measured with respect to the longitudinal axis 148, are substantially the same. (As used herein, the meanings of substantially and generally include their ordinary and customary meanings as well as being a certain percentage of a stated value e.g., 0.1% and 1%.) FIG. 10 shows another example of the surgical needle 100 in which a portion of the taper 155 projects, distally, a distance "P" beyond the periphery 140 of the bevel 115 when the stylet 110 is in the retracted position. The stylet tips of these examples reduce resistance of the surgical needle 100 through the tissue, as described in greater detail below.

Continuing with the example shown in FIG. 7A, the distal facing surface 161 of the first portion 160 is positioned such that it is outside of the hollow body 105, distal of the bevel 115, when the stylet 110 is in the extended position. In other examples, the distal facing surface 161 is positioned more proximally. When the stylet 110 is in the extended position, the distal facing surface 161 is inside the hollow body 105. In these examples, the second portion 165 (which may be made from an elastomeric material as described previously) extends beyond the bevel 115 while the first portion 160 remains sheathed by the hollow body 105. In some application, it is desirable that the portion of the stylet 110 that is exposed when the stylet 110 is in the extended position is completely made from an elastomeric material.

Returning to FIG. 6, a stylet hub 170 is disposed at the proximal end 111 of the stylet 110. The stylet hub 170 together with the opening 125 and passageway 127 of the needle hub 120 serve to couple the stylet 110 and hollow body 105 together (best seen in FIG. 2). The stylet hub 170 has a geometry (shape, size, length, etc.) suitable for being held in the surgeon's palm.

FIGS. 8A-8C show an example of the surgical needle 100 for conducting fluid from a joint space to an environment outside of the patient. When fluid exits the proximal end of the surgical needle 100, the surgeon knows that the distal end of the surgical needle 100 is in the joint space. The stylet 110 has an outer surface 175 extending between the distal region 146 and proximal region 147 of the elongated body 145. The outer surface 175 defines a port 180. The port 180 is positioned along a length of the outer surface 175, adjacent to the stylet tip 150, to minimize trauma. Generally, the port 180 is circular in shape (as shown) but could also be polygonal in shape. The port 180 may further include a chamfer disposed around the port to further minimize trauma.

The elongated body 145 further includes a fluid conduit (lumen) 185 inside. The fluid conduit 185 runs a length of the elongated body 145. A distal end of the fluid conduit 185 communicates with the port. When the stylet 110 is in the retracted position (for example when the surgical needle 100 is being pushed by tissue), the port 180 is covered by the hollow body 105. Effectively, the port 180 is closed off and no fluid can enter. When the stylet 110 is in the extended position (e.g., when the surgical needle 100 exits tissue and enters joint space), the port 185 is exposed. Fluid from the joint space enters the port 180 and fluid conduit 185, and eventually exits the surgical needle 100 through a drain at the proximal end of the fluid conduit 185.

FIG. 8B shows an example of the surgical needle 100 in which the fluid conduit 185 terminates in the stylet hub 170 (as shown) or beyond the stylet hub 170. A proximal end of the fluid conduit 185 is opened and fluid drains from an opening 186. The port 180, fluid conduit 185, and opening 186 form a passageway from the interior of the joint space to the environment exterior the patient.

FIG. 8C shows another example of the surgical needle 100 in which the outer surface 175 of the elongated body 145 defines a drain port 187. The drain port 187 is positioned within the needle hub 120 (e.g., within the passageway of the needle hub 120). The needle hub 120 includes a drain 121. The needle hub drain 121 and drain port 187 are in fluid communication. The port 180, fluid conduit 185, drain port 187, and needle hub drain 121 form a passageway from the interior of the joint space to the environment exterior the patient. FIGS. 9A and 9B show another example of the surgical needle 100 in which fluid flow enters the hollow body 105. The hollow body 105 has an outer surface 190 extending between the bevel 115 at the distal end and the needle hub 120 at the proximal end. The outer surface 190 defines a port 191. The port 191 is positioned along a length of the outer surface 190, adjacent to bevel 115, to minimize trauma. Generally, the port 191 is circular in shape (as shown) but could also be polygonal in shape, such as a triangle, square, and rectangle.

The example further includes a fluid conduit 195 formed from the outer surface 175 of the stylet 110 (shown as a flat portion along a length of the stylet 110) and an inner surface of the hollow body 105. Effectively, the fluid conduit 195 acts as a sliding valve for the port 191. When the stylet 110 is the extended position, the fluid conduit 195 slides in the distal direction, opening the valve and allowing fluid to enter the port 191. When the stylet 110 is in the retracted position, the fluid conduit slides in the proximal direction closing the valve inhibiting fluid from entering the port 191.

The fluid conduit 195 is in fluid communication with an annular space 196 between the inner surface of the hollow body 105 and stylet 110. Fluid entering the port 191 flows through fluid conduit 195 and into the annular space 196. In the example shown in FIG. 9B, the fluid flow is transmitted through the annular space 196 and exits through a drain 197 in the needle hub 120. In another example, similar to the one described above with reference to FIG. 8C, the fluid flow is transmitted inside the lumen of an elongated body and crosses through a side hole in the vicinity of a drain in a needle hub.

Some examples of the stylet tip 150 are resistance reducing members. The resistance reducing member has a shape or profile that when the stylet 110 is in the extended position, the resistance reducing member is in contact of the tip 130 of the bevel 115 and protects the tissue from being cut/penetrated by the tip 130. When the stylet 110 is in the retracted position, the resistance reducing member reduces resistance of the surgical needle 100 through the tissue, as quantified below with reference to FIGS. 11A-11C.

The resistance to the surgical needle 100 (i.e., hollow body 105 and stylet 110) advancing through tissue can be divided into two primary contributors:

1) The amount (area) that a resistance reducing member fills the hollow needle at the bevel 115.

2) The likelihood for tissue to be caught rather than slide by the resistance reducing member/needle tip interface.

If either contributor is below a threshold, then the surgical needle 100 does not exhibit reduced resistance. There is a range of varying resistance reduction if either one of the contributors is below a threshold.

1) Area

To quantify the resistance reducing member fill, a ratio of resistance reducing member cross sectional area (A resistance reducing member) divided by the total hollow body inside diameter area (A hollow body ID) can be obtained. For consistency, these areas are viewed from the distal end of the hollow body 105 and represent the section taken in the plane of the bevel 115.

$$\text{Reduced resistance} = A \text{ resistance reducing member}/A \text{ hollow body ID} > \sim 0.7$$

2) Tissue Catching

Figure 11A:
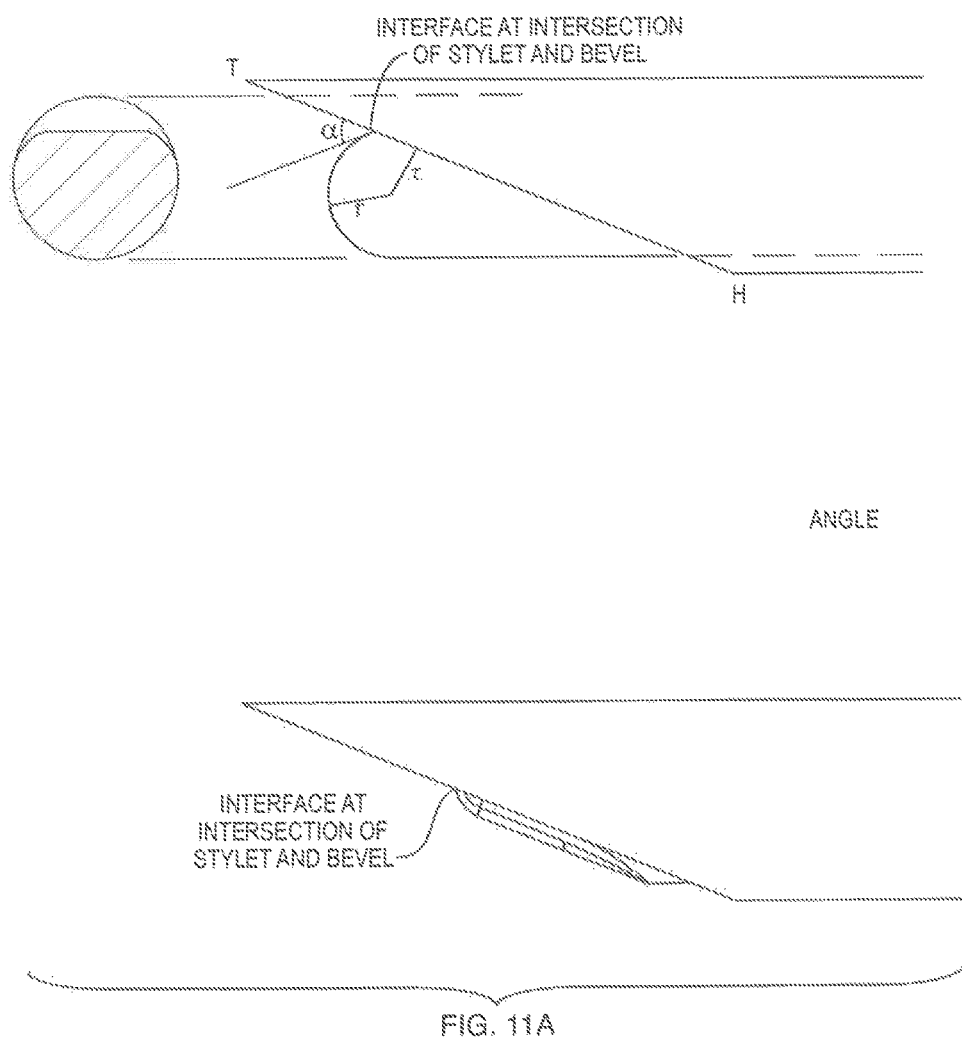
FIGS. 11A-11C show examples of a resistance reducing member.
Figure 11B:
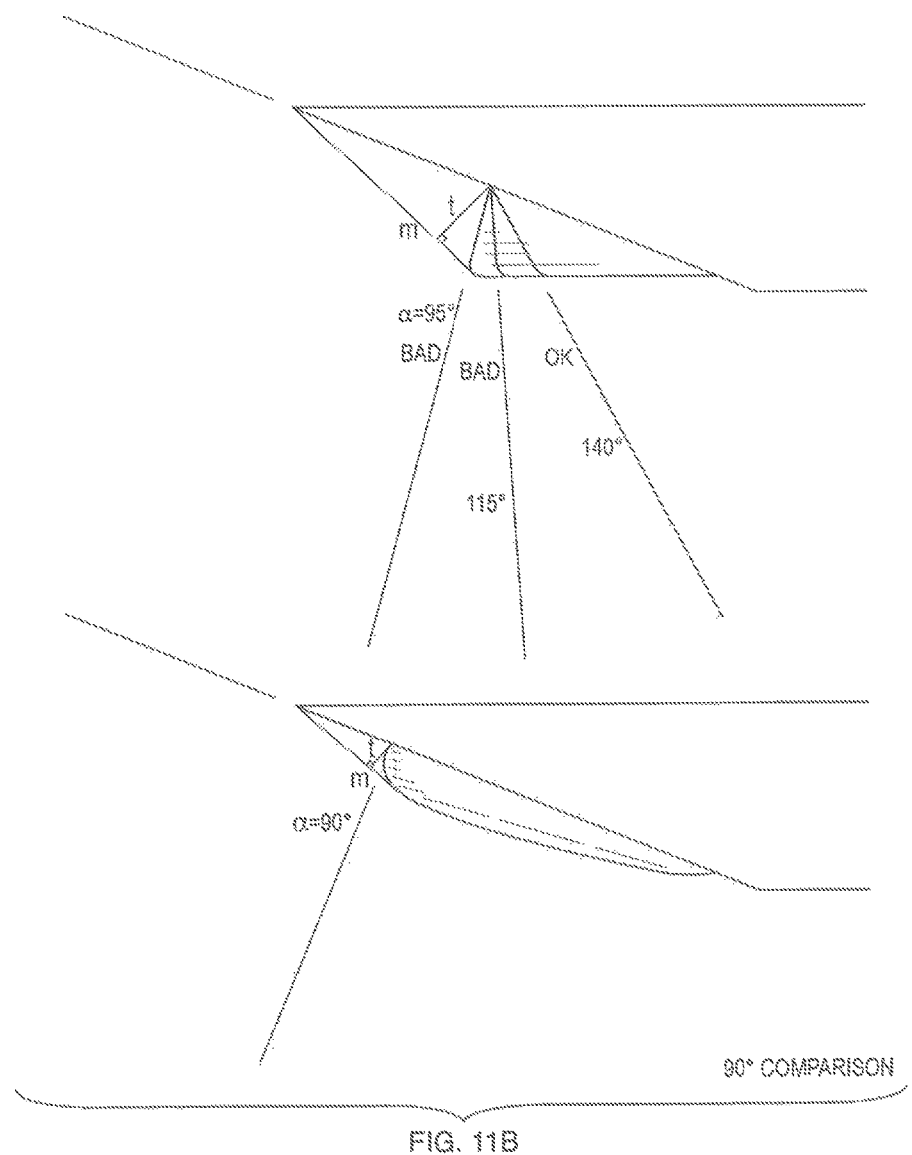

Angle: If the resistance reducing member protrudes distally from the bevel 115, then an angle $\alpha$ can be drawn between the bevel 115 and a first tissue contacting edge of the resistance reducing member as shown in FIG. 11A. (In the examples described with reference to FIGS. 7A and 7B, the distal terminus 151 forms at least a portion of the first tissue contacting edge.) The intersection of the bevel 115 and first tissue contacting edge of the resistance reducing member is called the interface. The angle $\alpha$ of the interface gives a first indication as to the likelihood that tissue will be caught between the bevel 115 and resistance reducing member. An acute angle is more likely to catch tissue than an obtuse angle. However, the angle alone does not fully describe the protrudence of the stylet 110 as is shown in FIG. 11B, which illustrates two similar angles that have differing likelihoods to catch tissue.

A measure of the protrudence may take the form of a ratio of stylet geometry that describe the roundness of the first portion of the resistance reducing member to encounter tissue as it slides along the bevel 115. FIG. 11A shows the distal radius, r, of the resistance reducing member as well as the perpendicular distance of the center of such radius to the bevel 115, $\tau$. A roundness ratio of $\tau/r$ will give an indication of the ability for tissue to catch on a curved versus relatively flat member.

Figure 11C:
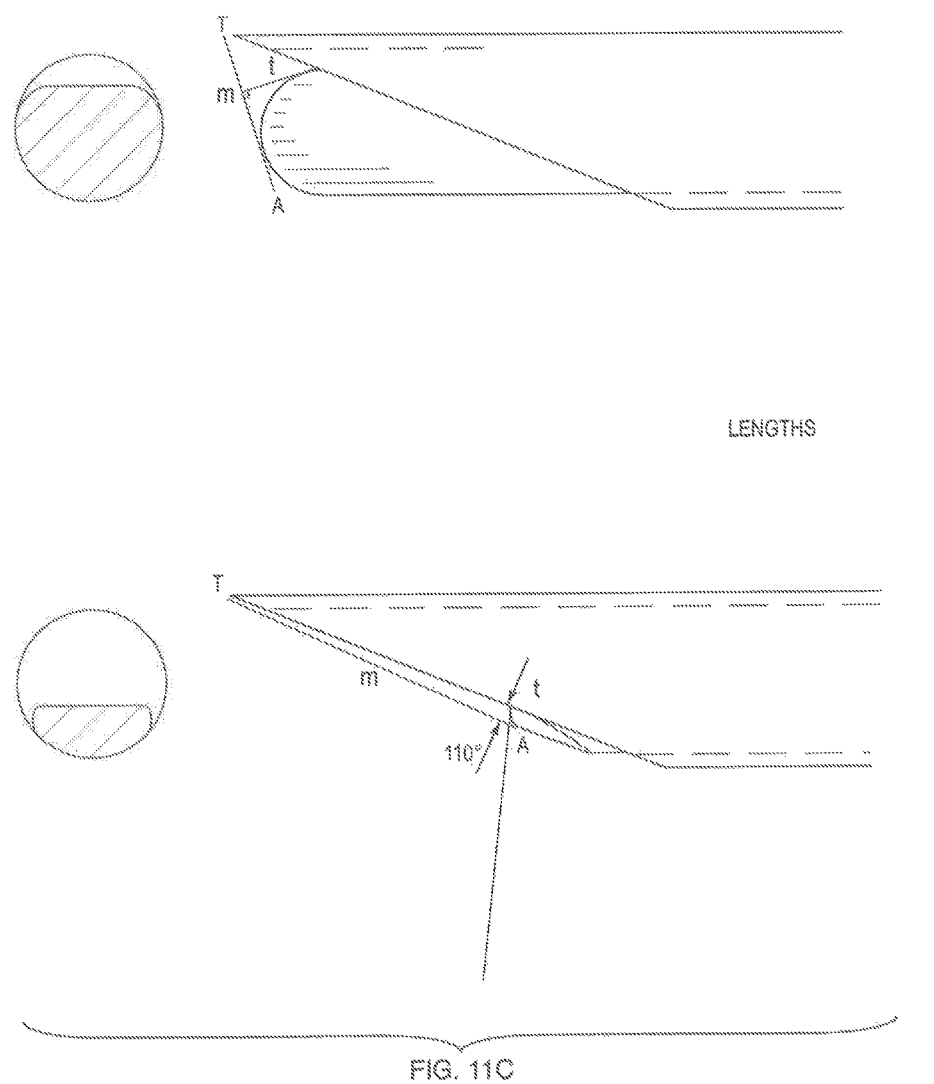
Figure 12C:
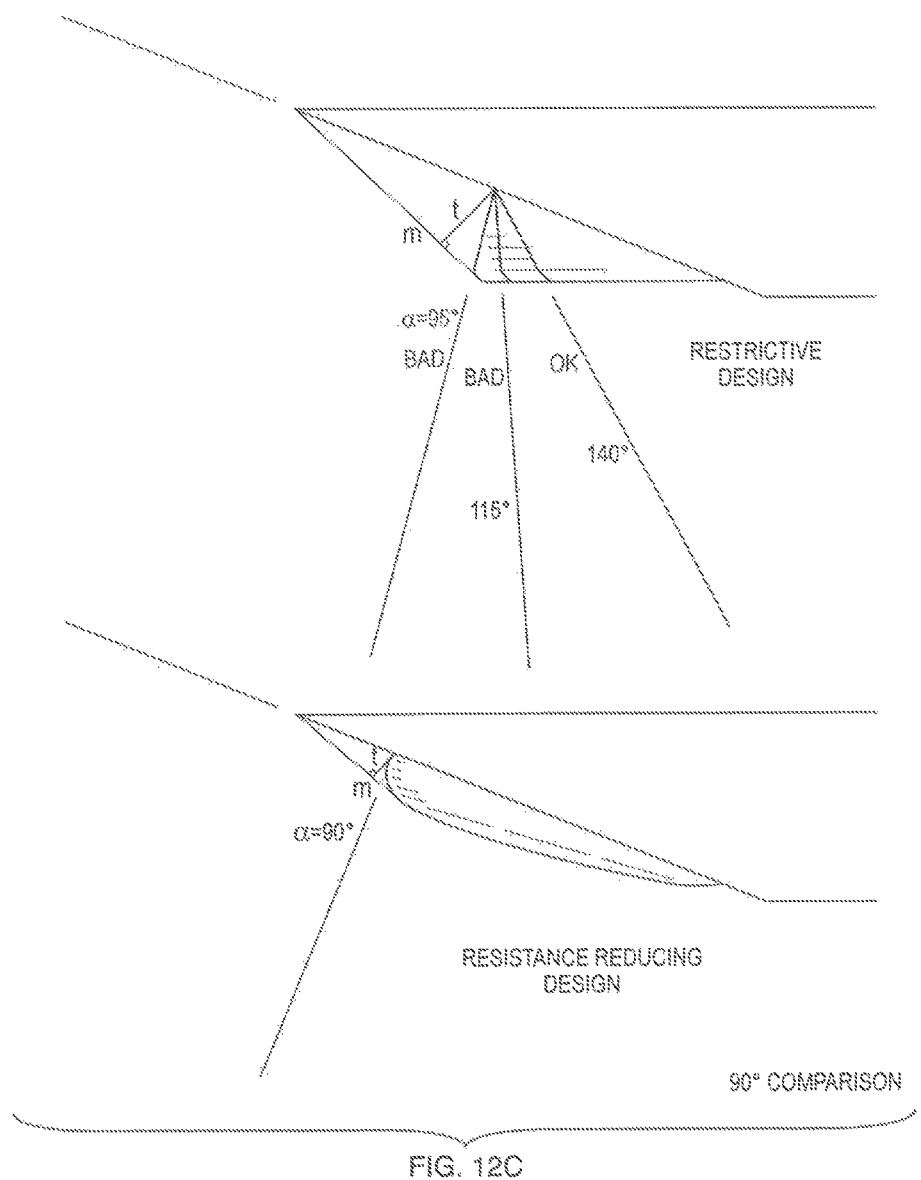
Figure 12D:
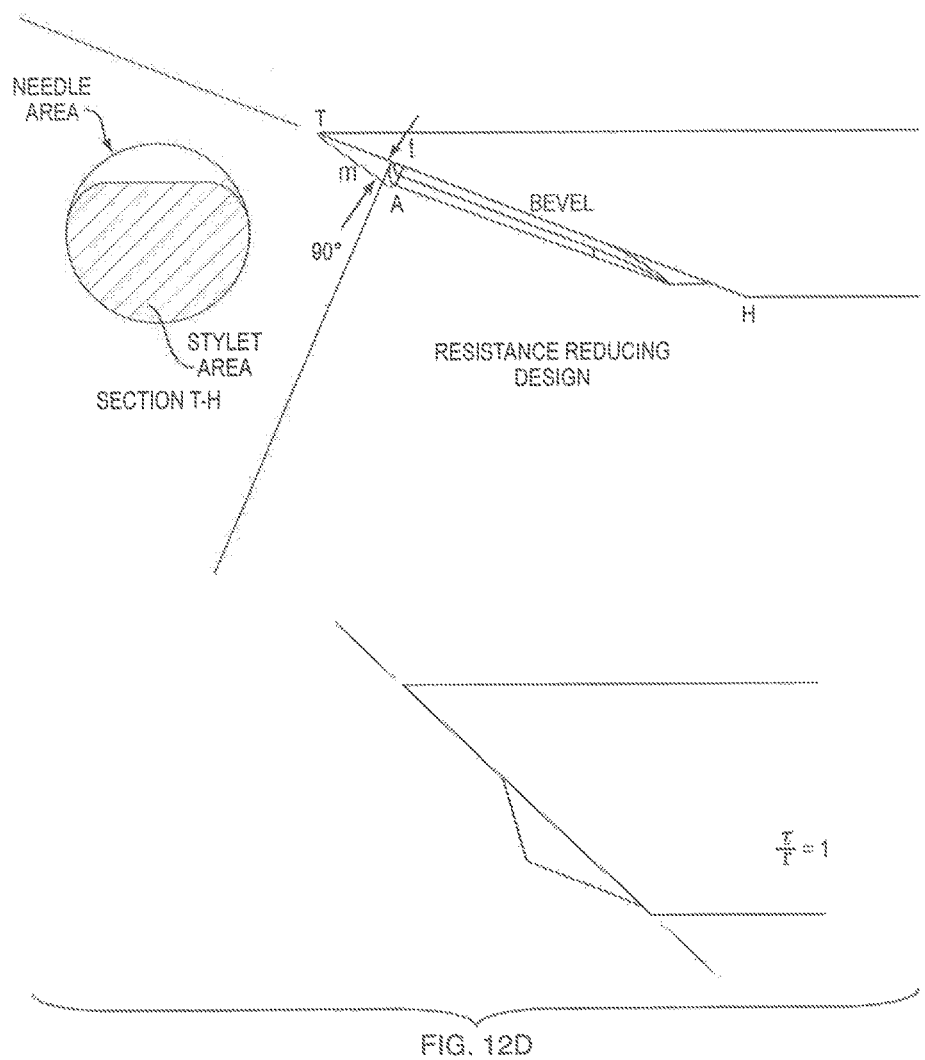
Figure 12E:
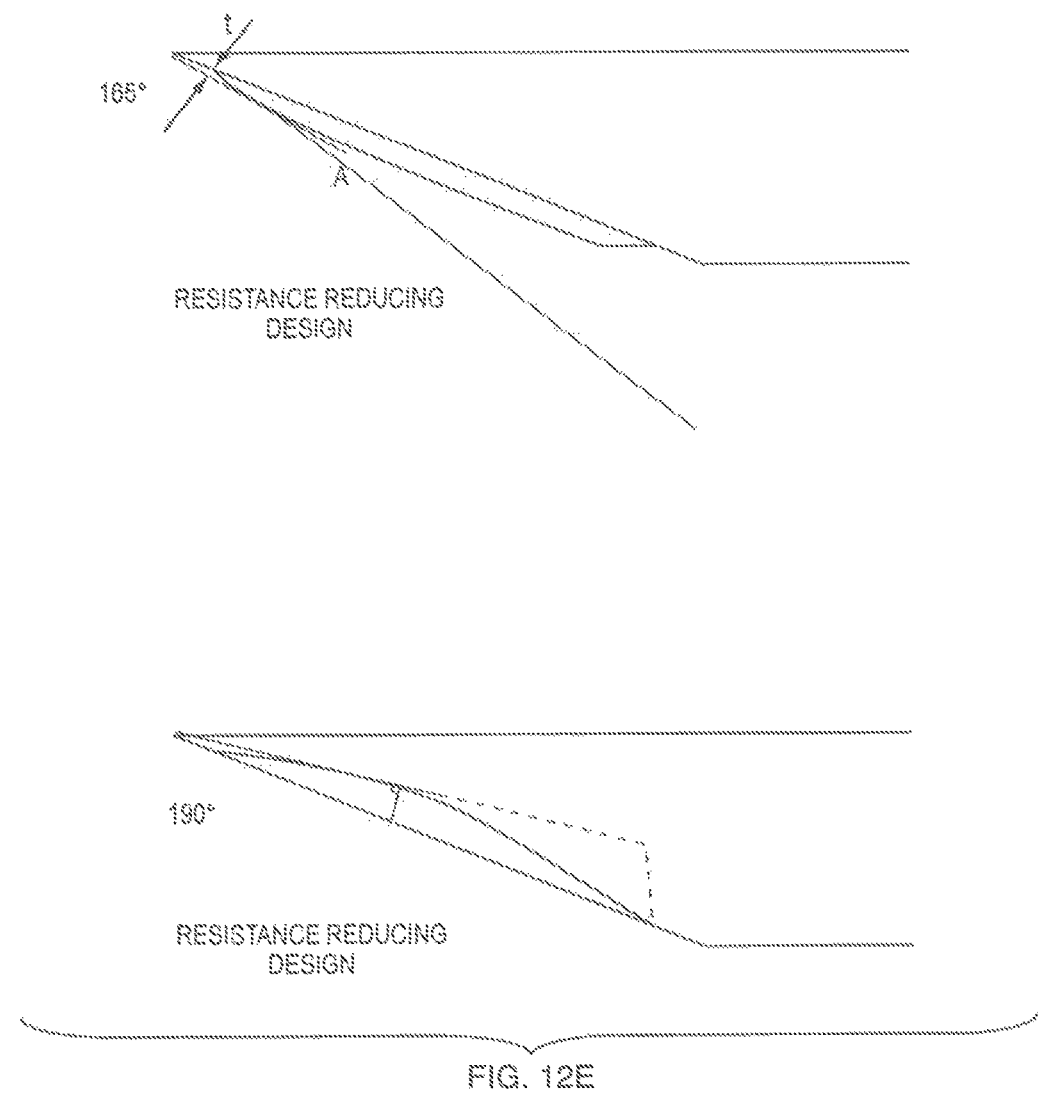

The angle, $\alpha$ may be modified by a roundness ratio to convey their combined effects, $\alpha'$.

$$\text{Reduced resistance} = \alpha' = \alpha - k(\tau/r) > \sim 90°,$$

where k=a multiplier of the roundness affect that helps distinguish the crossover to resistance reduction (eg., k~4). Lengths: Another measure of protrudence may be obtained by the ratio of geometry that describes the tissue catching area. FIG. 11C shows the length m to be between tip T and the most distant portion of the resistance reducing member measured perpendicularly from the bevel 115. A line t is created perpendicular to line m, such that t intersects the point where the bevel 115 and resistance reducing member cross (i.e., the interface). A mouth ratio of t/m gives an another indication to the likelihood that tissue will be caught between the bevel 115 and resistance reducing member $$\text{Reduced resistance} = t/m \sim < 0.25$$

Other designs are possible, such as those shown in FIGS. 12A-12E (which also shows examples of resistive designs). Other examples of the resistance reducing member have a reduced resistance coating to further lower the resistance of the surgical needle 100 through tissue.

FIGS. 13A-13E show an example procedure for entering a joint space through tissue using an example of the surgical needle 100 with an elastomeric tip as described above. Each of the figures includes a close up view of the distal end 101 of the surgical needle 100. Of particular note is correspondence between position of the stylet 110 and progress of the surgical needle 100.

Figure 13A:
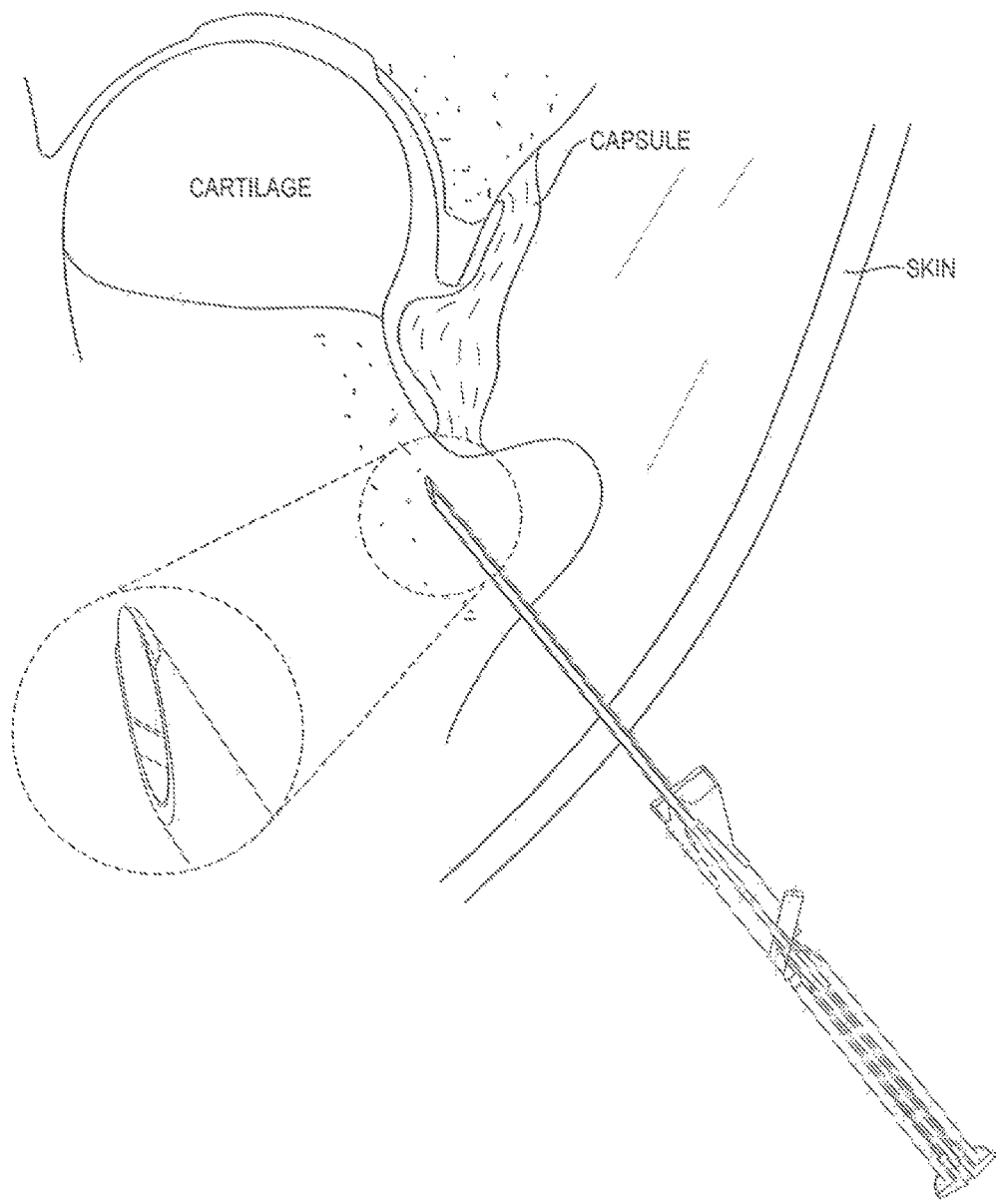
FIGS. 13A-E are views of a procedure for entering a joint space through tissue using an example of the surgical needle with an elastomeric tip.

FIG. 13A shows the surgeon pushing the surgical needle 100 through tissue along an initial trajectory. The stylet 110 is retracted exposing the cutting/penetrating tip 130 to the tissue. The elastomeric tip completely fills the area of the hollow body 105 at the bevel 115. The surgeon uses less force to push the surgical needle 100 through the tissue because the resistance is reduced relative to the area being partially or completely unfilled. The initial trajectory, however, is wrong and the surgical needle 100 will miss the preferred joint entry point.

Figure 13B:
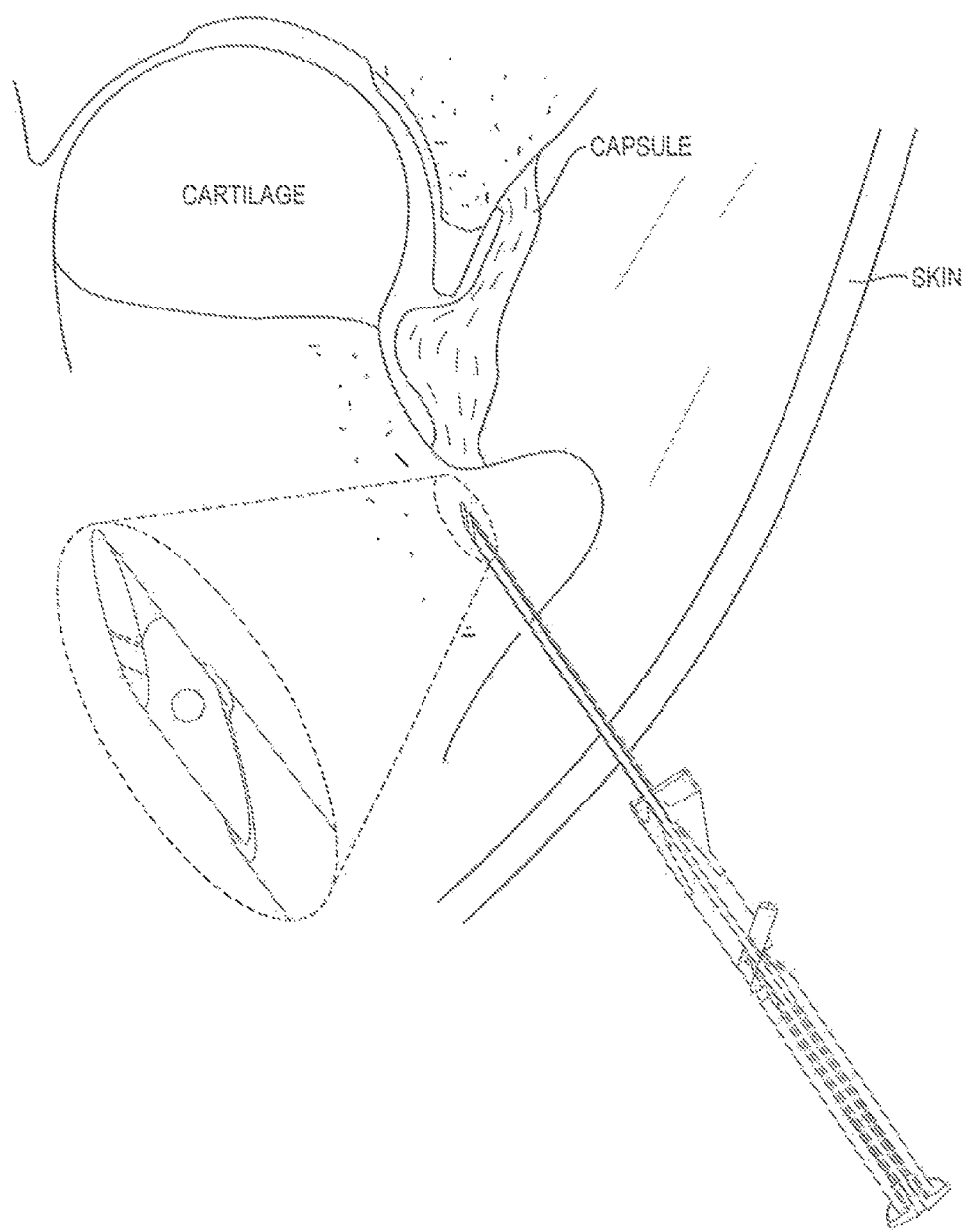

FIG. 13B shows the surgeon pulling the surgical needle 100 back. In the absence of tissue pushing against the stylet 110 it extends.

Figure 13C:
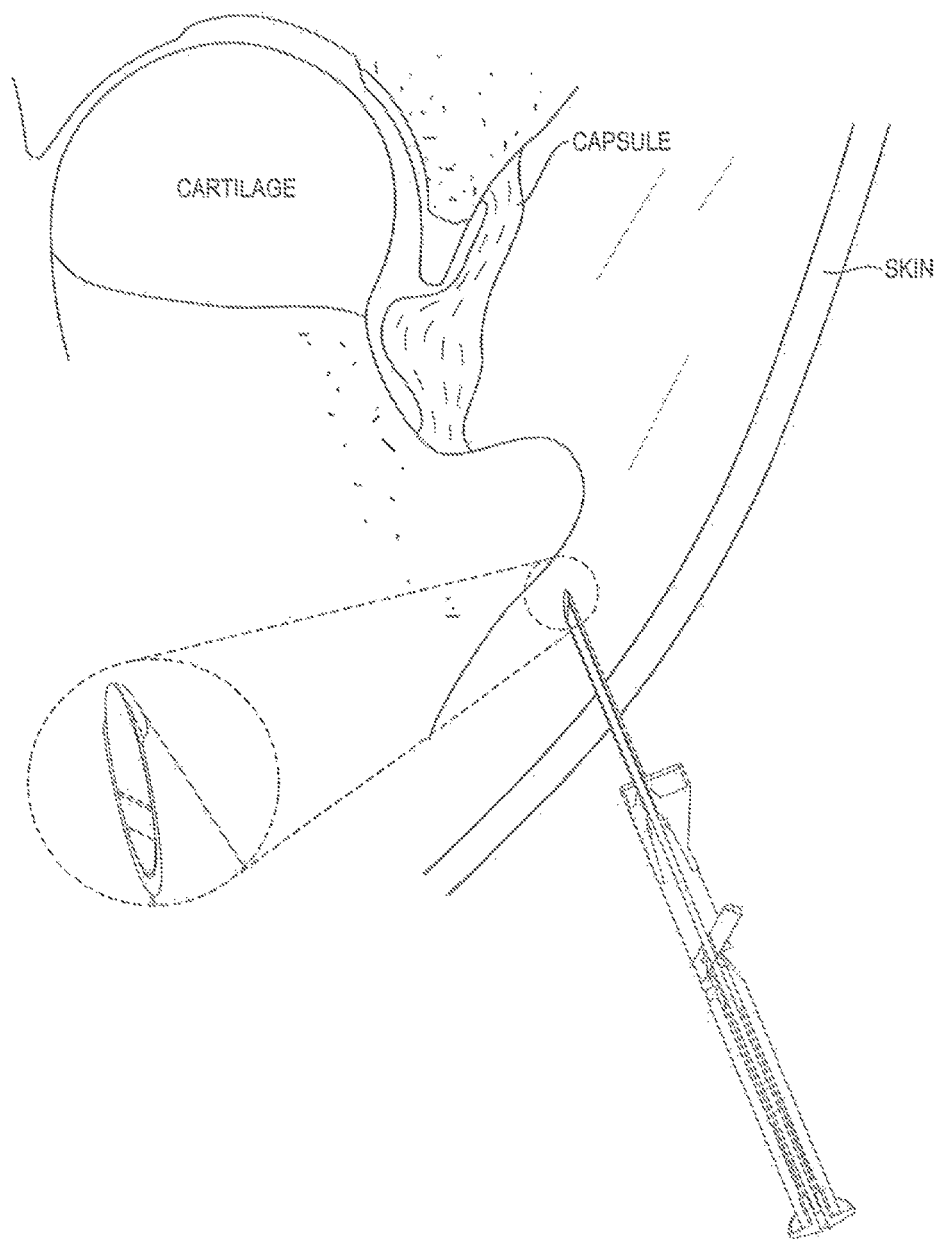

FIG. 13C shows the surgeon redirecting the surgical needle 100 with the stylet 110 in retracted position and the cutting/penetrating tip 130 exposed. The surgeon typically repeats the foregoing steps of pushing and pulling several times during the procedure. This is referred to as "pistoning."

Figure 13D:
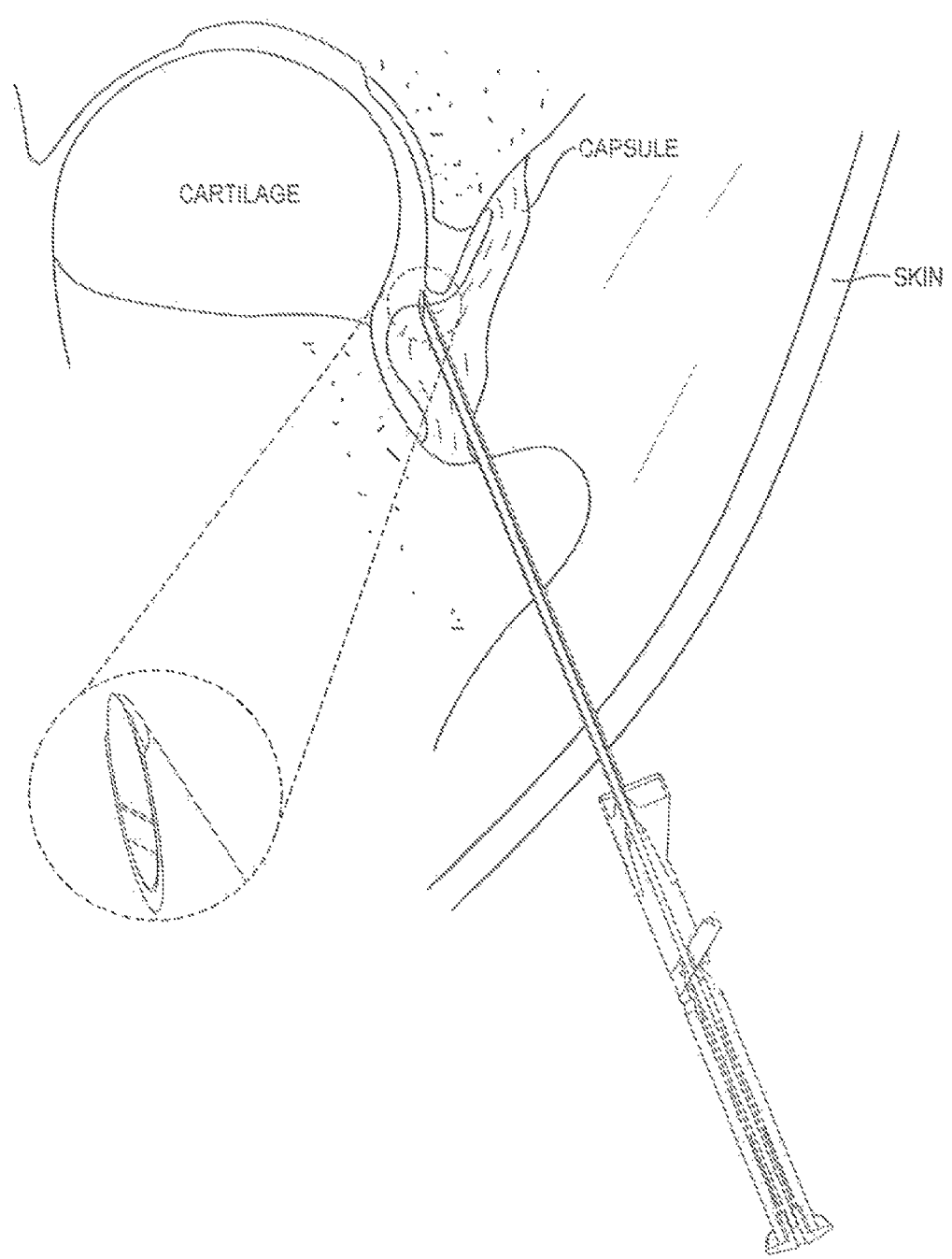

FIG. 13D shows the surgeon pushing the surgical needle 100 through the capsule. The stylet 110 is the retracted position, the cutting/penetrating tip 130 exposed, and the elastomeric tip completely fills the area of the hollow body 105 at the bevel 115. The femoral head with delicate cartilage is very close to where the bevel 115 is about to exit the capsule, completely.

Figure 13E:
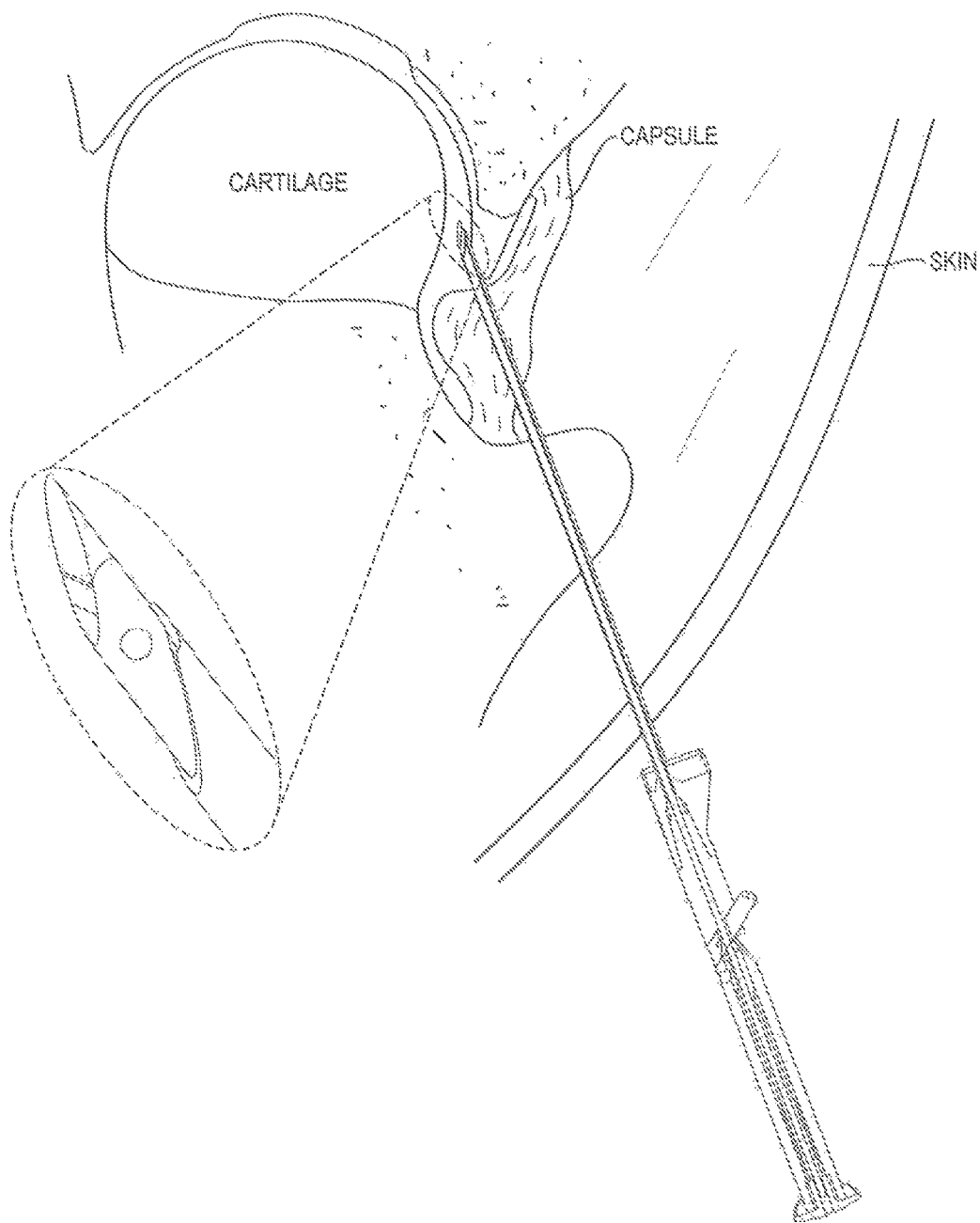

FIG. 13E shows the surgeon pushing surgical needle 100 so that that the bevel 115 is completely through the capsule and in the joint space. In the absence of tissue pushing against the stylet 110, the stylet 110 extends. Extension of the stylet 110 exposes the port in the side of the stylet 110. Fluid from the joint space enters the port and the fluid conduit, and subsequently, the surgeon sees or feels the fluid emptying from the drain in the needle hub 120. The surgeon knows that the distal end of the surgical needle 100 has progressed into the joint space and stops pushing the surgical needle 100. Should the surgeon continue pushing the surgical needle 100 and contact the articular cartilage and femoral head by accident, the elastomeric tip minimizes or prevents damage to them.

In the foregoing example, the joint space is the hip joint. The hip example is but one example and is not limiting. Procedures for entering other joint spaces, such as the shoulder or ankle, are similar.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described examples, but should be defined only in accordance with the following claims appended hereto and their equivalents.

What is claimed is:

1. A surgical needle for entering a joint space through tissue, the surgical needle comprising:
   a hollow body with a bevel, a periphery of the bevel defining an open area at the bevel; and
   a stylet movable within the hollow body between an extended position and a retracted position, the stylet comprising
      an elongated body having a closed distal region and a proximal region, the elongated body comprising a non-deformable first material;
      a tip formed with the elongated body, the tip extending from the distal region of the elongated body and terminating at a distal terminus, the distal terminus being axially aligned with the elongated body and defining a distal-most end of the stylet; and
      a taper extending between the distal terminus and a point proximal to the distal terminus, at least a portion of the taper filling in the open area at the bevel when the stylet is in the retracted position,
   wherein the tip comprises a first portion extending a longitudinal length, distally, from the distal region of the elongated body and terminating at a distal facing surface, and
   wherein the tip comprises a second portion extending between the distal facing surface and the distal terminus, the second portion of the tip comprising a deformable second material.

2. The surgical needle of claim 1, wherein the non-deformable first material is any one of metal and non-metal.

3. The surgical needle of claim 1, wherein the deformable second material is reversibly deformable.

4. The surgical needle of claim 3, wherein the reversibly deformable second material is an elastomer.

5. The surgical needle of claim 1, wherein the first portion and second portion of the tip comprise an elastomeric material.

6. The surgical needle of claim 1, wherein a portion of the taper projects, distally, beyond the periphery of the bevel when the stylet is in the retracted position.

7. The surgical needle of claim 1, wherein the taper is flush with the periphery of the bevel when the stylet is in the retracted position.

8. The surgical needle of claim 1, wherein the second portion of the tip comprises a proximal facing surface in contact with the distal facing surface of the first portion of the tip.

9. The surgical needle of claim 1, wherein the distal facing surface of the first portion is bonded to the second portion with an adhesive.

10. The surgical needle of claim 1, wherein the second portion of the tip is molded over the distal facing surface of the first portion of the tip.

11. The surgical needle of claim 1, wherein the taper is at an acute angle to a longitudinal axis extending between the distal region and the proximal region of the elongated body.

12. The surgical needle of claim 1, further comprising:
   a needle hub disposed at an end of the hollow body opposite the bevel; and a stylet hub disposed at the proximal region of the elongated body, the stylet hub and needle hub cooperatively coupling the stylet and the hollow body together.

13. The surgical needle of claim 1, wherein the stylet further comprises:
   a lumen through the elongated body, the lumen opened at the proximal region of the elongated body and closed at the distal region of the elongated body;
   an outer surface extending between the proximal region and the distal region of the elongated body; and
   a port in the outer surface and adjacent to the tip.

14. The surgical needle of claim 13, further comprising:
   a needle hub disposed at a region of the hollow body opposite of the bevel; and
   a stylet hub disposed at the proximal region of the elongated body, the stylet hub and needle hub cooperatively coupling the stylet and hollow body together,
   wherein the needle hub comprises an opening in fluid communication with the lumen at the proximal region of the elongated body which permits fluid to drain out from the surgical needle.

15. The surgical needle of claim 13, further comprising:
   a needle hub disposed at an end of the hollow body opposite of the bevel; and
   a stylet hub disposed at the proximal region of the elongated body, the stylet hub and needle hub cooperatively coupling the stylet and hollow body together, wherein the stylet hub comprises an opening in fluid communication with the lumen at the proximal region of the elongated body which permits fluid to drain out from the surgical needle.

16. The surgical needle of claim 1, wherein the stylet further comprises an outer surface extending a partial length, distally, from the proximal region of elongated body, the outer surface of the stylet and an inner surface of the hollow body form a fluid conduit, and wherein the hollow body further comprises a port in an outer surface of the hollow body and adjacent to the bevel, the port in fluid communication with the fluid conduit which permits joint fluid to flow into the fluid conduit at the distal region of the elongated body and flow out of the fluid conduit at the proximal region of the elongated body.

17. The surgical needle of claim 16, wherein the outer surface of the stylet comprises a flat portion formed in the outer surface of the stylet.

\* \* \* \* \*